US010182881B2

(12) United States Patent
Monty et al.

(10) Patent No.: US 10,182,881 B2
(45) Date of Patent: Jan. 22, 2019

(54) DENTAL LASER APPARATUS AND METHOD OF USE WITH INTERCHANGEABLE HAND PIECE AND VARIABLE FOOT PEDAL

(71) Applicant: Convergent Dental, Inc., Natick, MA (US)

(72) Inventors: Nathan P. Monty, Shrewsbury, MA (US); Charles H. Dresser, Bethel, ME (US); William H. Groves, Jr., Arlington, MA (US); Leonid A. Bafitos, Natick, MA (US); Jon R. Quillard, Carlisle, MA (US)

(73) Assignee: Convergent Dental, Inc., Needham, MA (US)

( * ) Notice: Subject to any disclaimer, the term of this patent is extended or adjusted under 35 U.S.C. 154(b) by 0 days.

(21) Appl. No.: 14/172,562

(22) Filed: Feb. 4, 2014

(65) Prior Publication Data
US 2014/0363784 A1 Dec. 11, 2014

Related U.S. Application Data

(60) Provisional application No. 61/761,020, filed on Feb. 5, 2013, provisional application No. 61/793,006, filed on
(Continued)

(51) Int. Cl.
*A61B 18/18* (2006.01)
*A61C 1/00* (2006.01)

(52) U.S. Cl.
CPC .......... *A61C 1/0046* (2013.01); *A61C 1/0023* (2013.01); *A61C 1/0061* (2013.01)

(58) Field of Classification Search
CPC ............................................ A61N 2005/0606
(Continued)

(56) References Cited

U.S. PATENT DOCUMENTS 4,580,557 A * 4/1986 Hertzmann ............ A61B 18/20
219/121.61
5,388,987 A * 2/1995 Badoz et al. ................ 433/29
(Continued)

FOREIGN PATENT DOCUMENTS

JP 5-344979 12/1993
WO WO-2009090645 A2 7/2009

OTHER PUBLICATIONS

International Search Report and Written Opinion for International Patent Application No. PCT/US2014/014674 dated Sep. 30, 2014, (15 pages).
(Continued)

*Primary Examiner* — John R Downey
(74) *Attorney, Agent, or Firm* — Goodwin Procter LLP

(57) ABSTRACT

A dental laser system for treatment of hard and/or soft tissue includes a main chamber housing optical and primary fluid supply subsystems, for directing a laser beam and fluid to a treatment area. A hand piece affixable to the main chamber, includes mating optical and secondary fluid supply subsystems. The hand piece can be rotatable or re-orientable about an optical axis within the hand piece. A lock can maintain a selectable angular orientation of the hand piece relative to the main chamber. A coupling can maintain a fluidic communication between the primary and secondary fluid supply subsystems even when the hand piece is rotated or re-oriented. A sensor and controller can sense a selected angular orientation of the hand piece and adjust the main optical subsystem according to the sensed angular orientation, to align the two optical subsystems. The laser may be controlled using a variable speed foot pedal.

30 Claims, 27 Drawing Sheets

Related U.S. Application Data on Mar. 15, 2013, provisional application No. 61/909,929, filed on Nov. 27, 2013.

(58) Field of Classification Search
USPC .................................................. 607/88–95
See application file for complete search history.

(56) References Cited

U.S. PATENT DOCUMENTS

| | | | |
|---|---|---|---|
| 5,738,678 A * | 4/1998 | Patel | 606/10 |
| 6,156,030 A | 12/2000 | Neev | |
| 2002/0183726 A1* | 12/2002 | Elbrecht et al. | 606/6 |
| 2004/0097910 A1* | 5/2004 | Brugger et al. | 606/10 |
| 2005/0288745 A1* | 12/2005 | Andersen | A61F 9/00781 607/86 |
| 2007/0104419 A1 | 5/2007 | Rizoiu et al. | |
| 2008/0262577 A1* | 10/2008 | Altshuler et al. | 607/89 |
| 2009/0049522 A1* | 2/2009 | Claus et al. | 726/4 |
| 2009/0093798 A1* | 4/2009 | Charles | A61F 9/008 606/4 |
| 2010/0015576 A1 | 1/2010 | Altshuler et al. | |
| 2011/0206072 A1* | 8/2011 | Karavitis | 372/25 |
| 2011/0229841 A1 | 9/2011 | Hamada | |

OTHER PUBLICATIONS

Notice of Reasons for Rejection in Japanese Patent Application No. 2015-556232 dated Jan. 31, 2018, 16 pages.

* cited by examiner

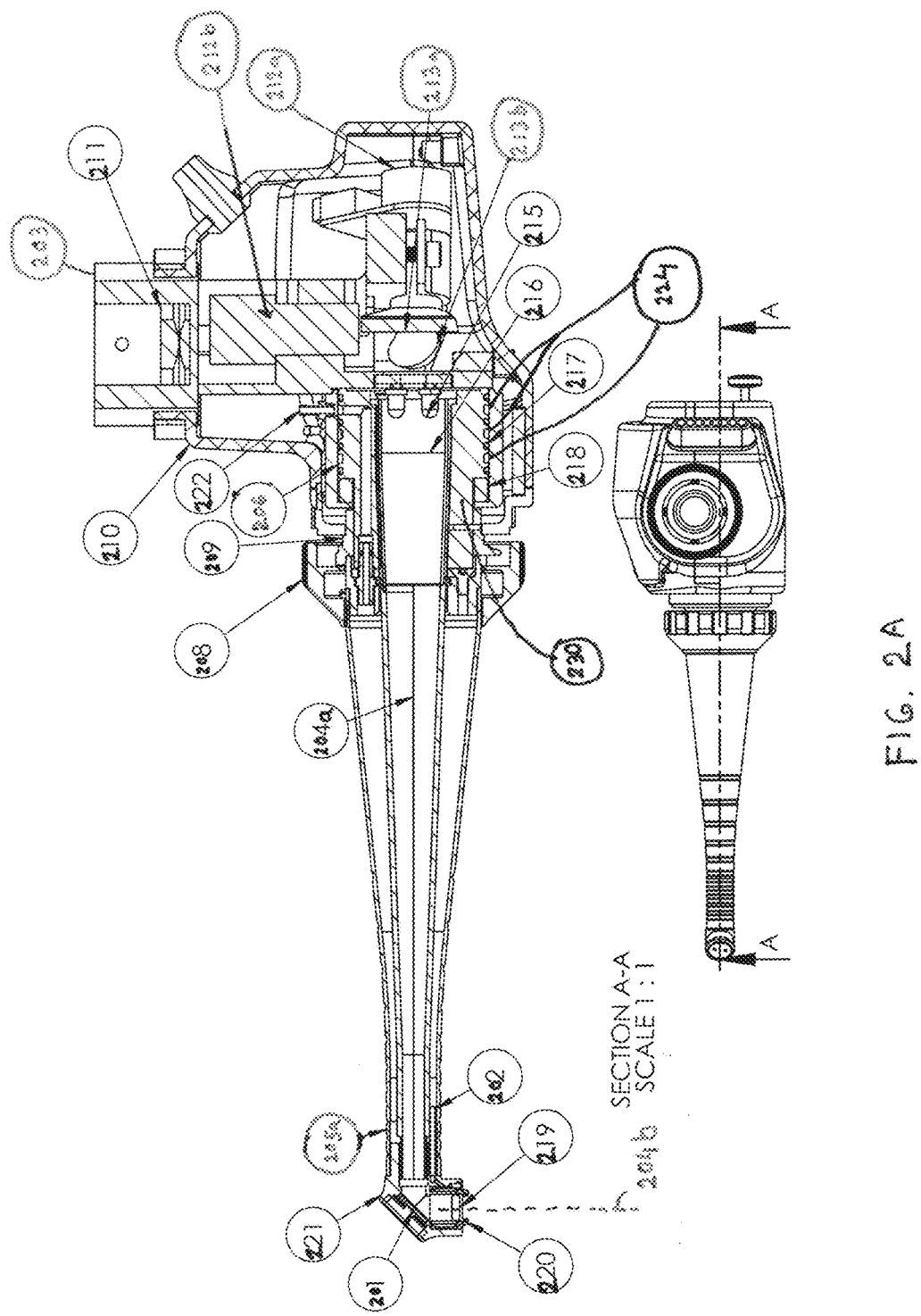

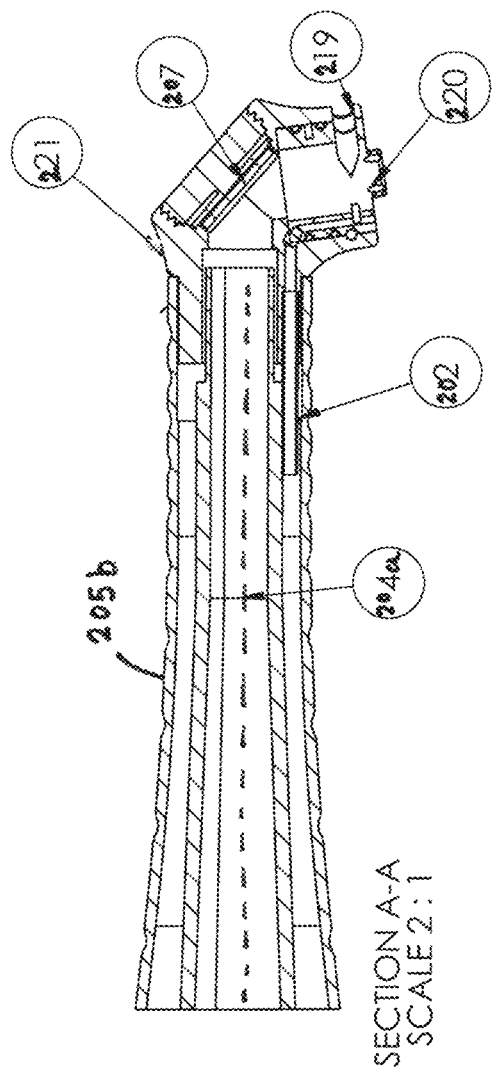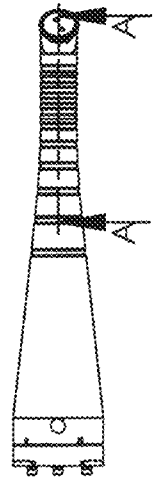
FIG. 2B

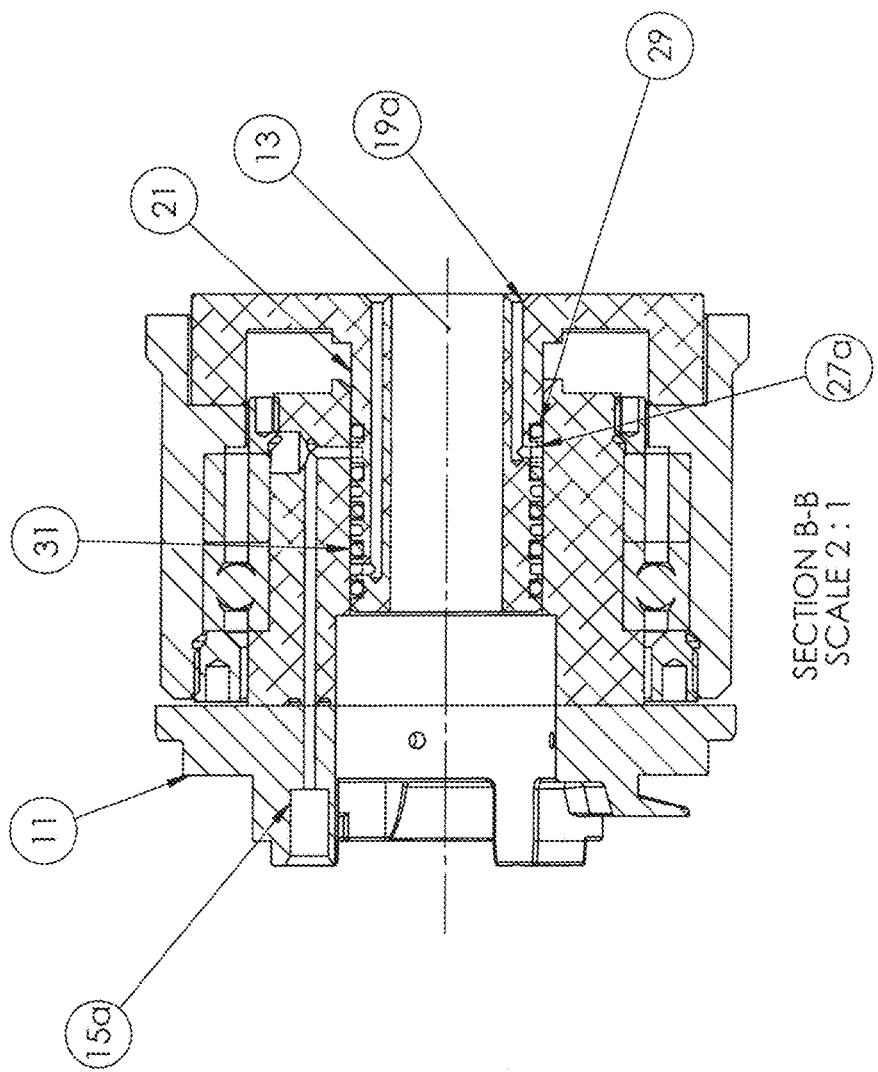
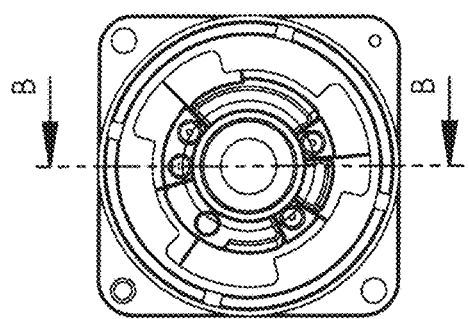
FIG. 3B

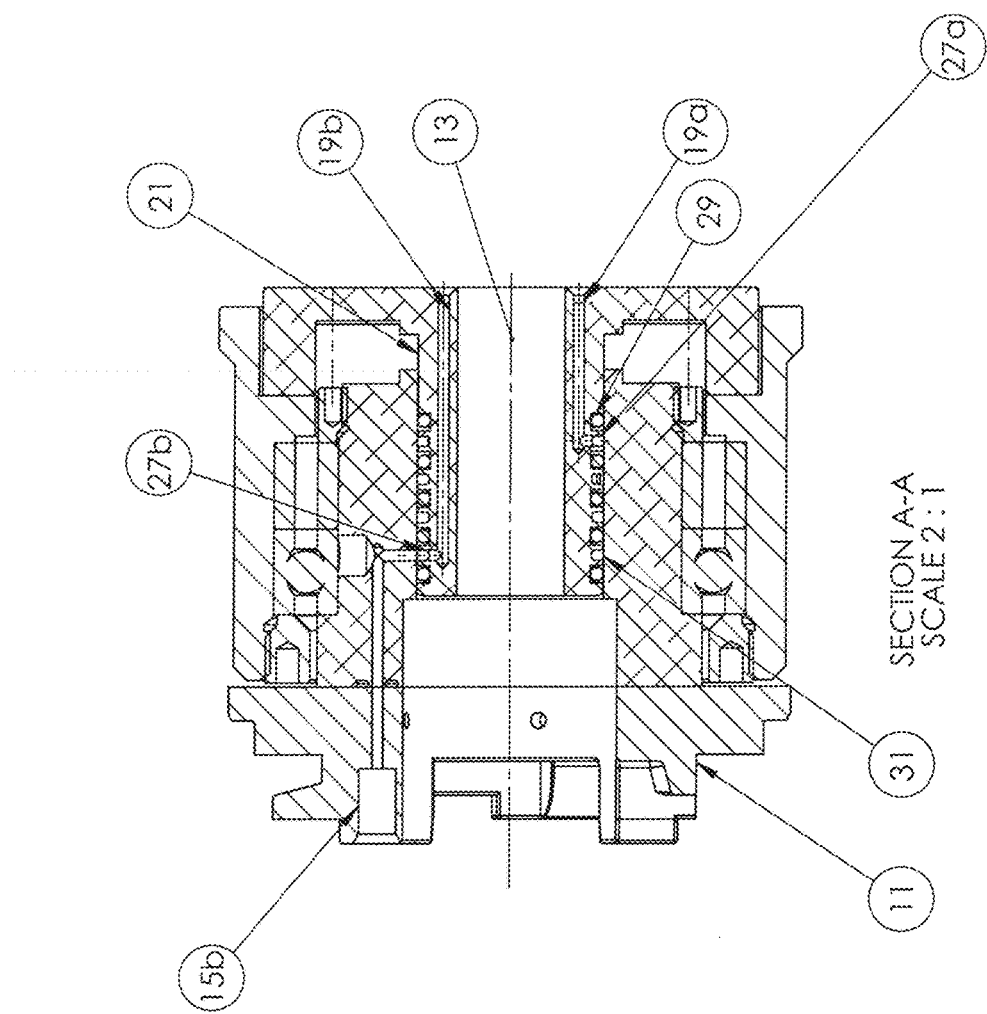
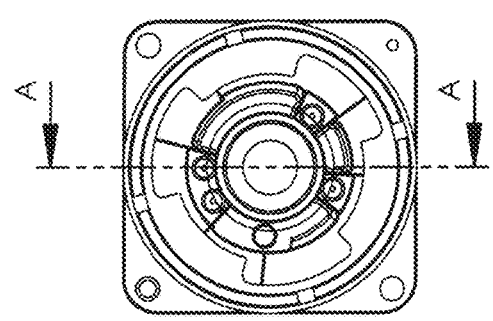
SECTION A-A
SCALE 2:1
FIG. 3C

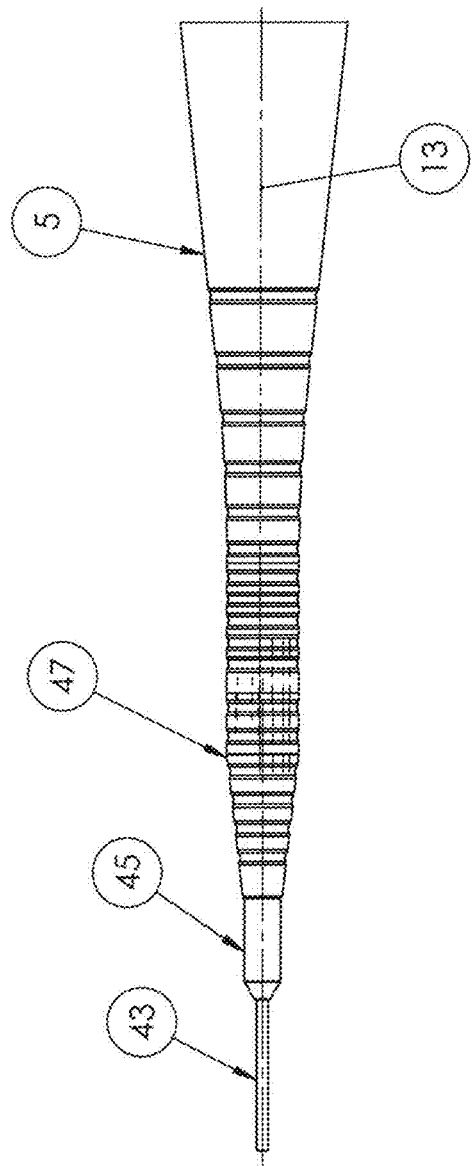

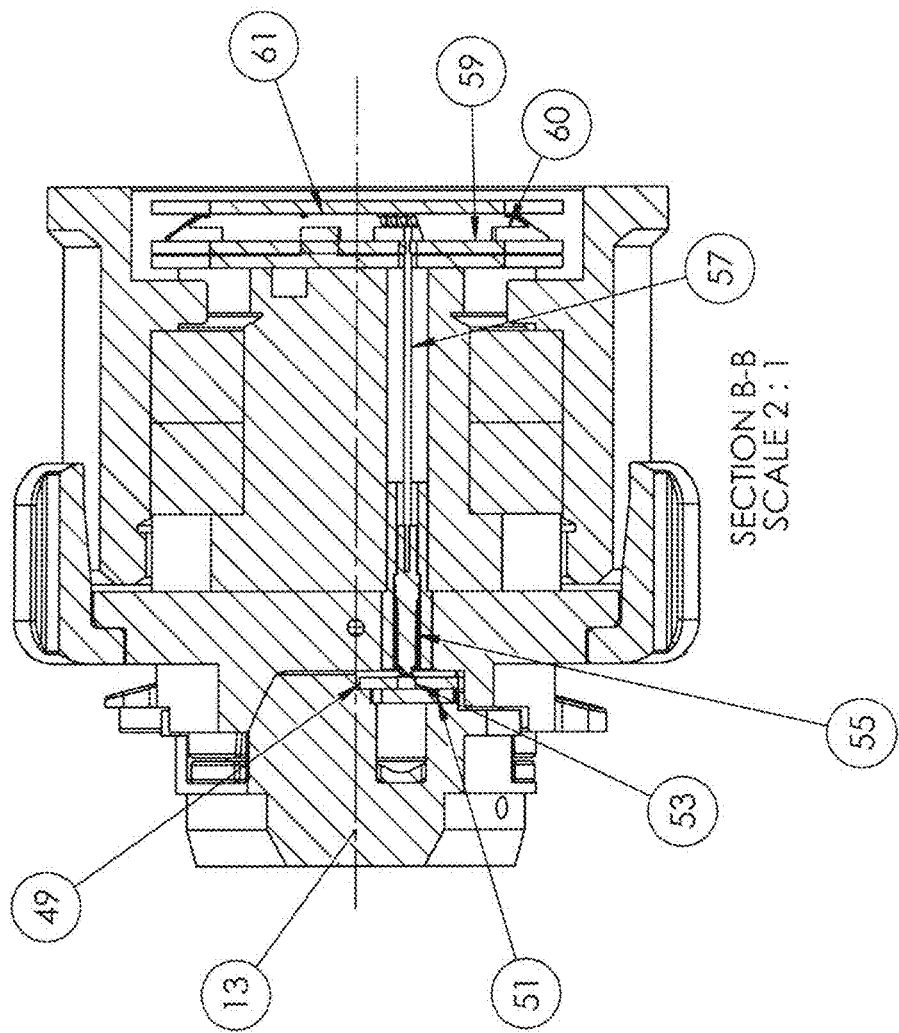
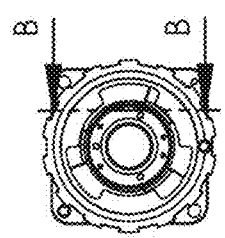
FIG. 5B

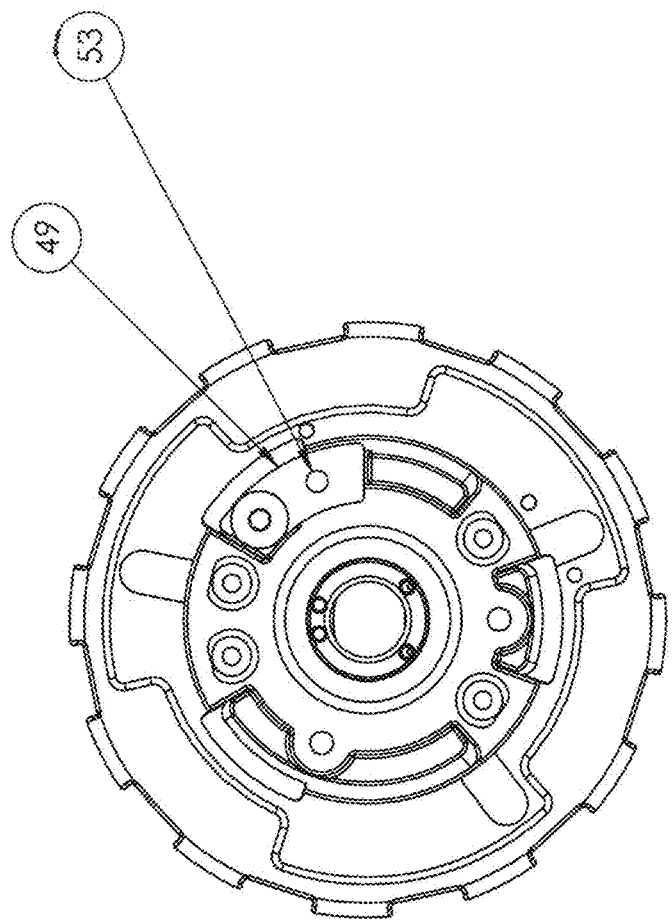

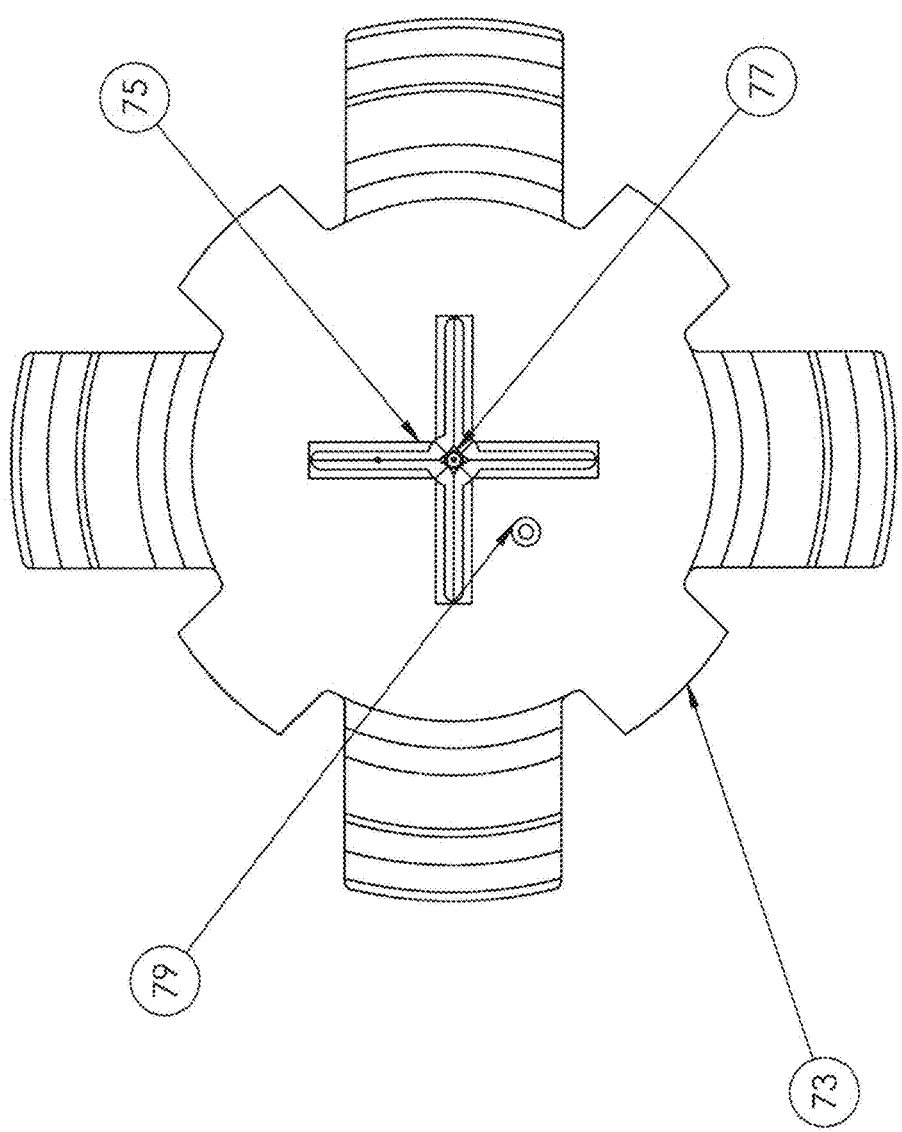

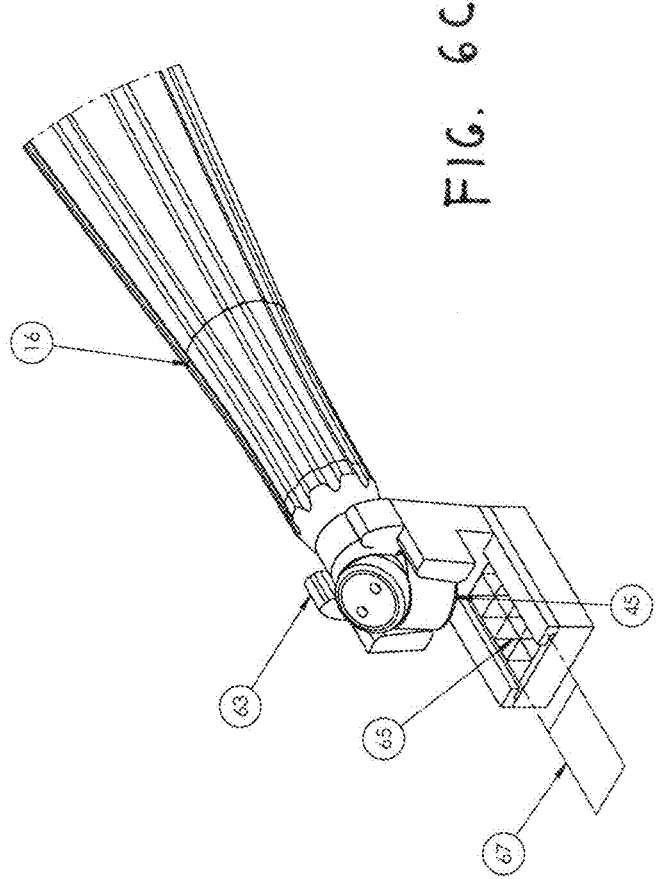

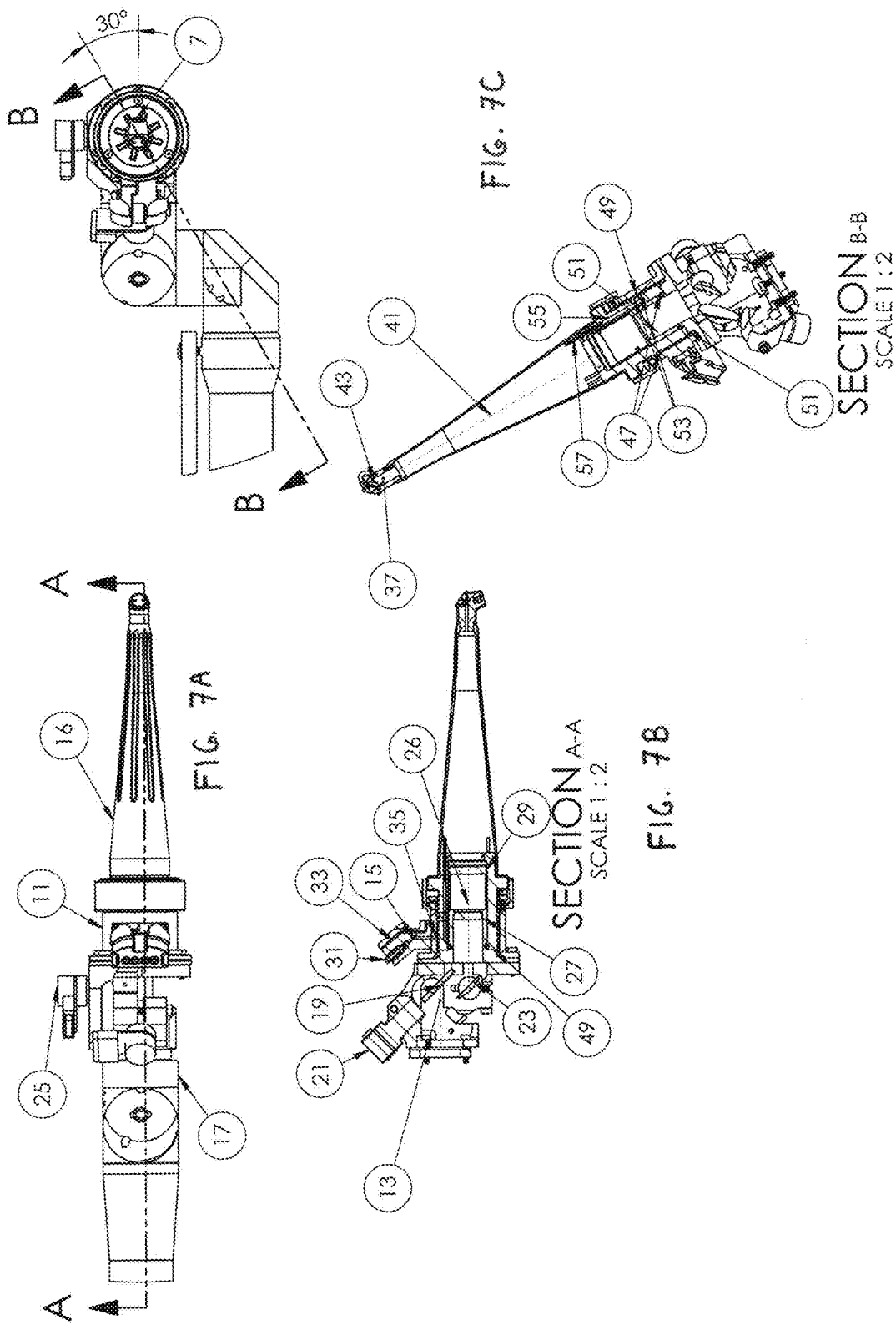

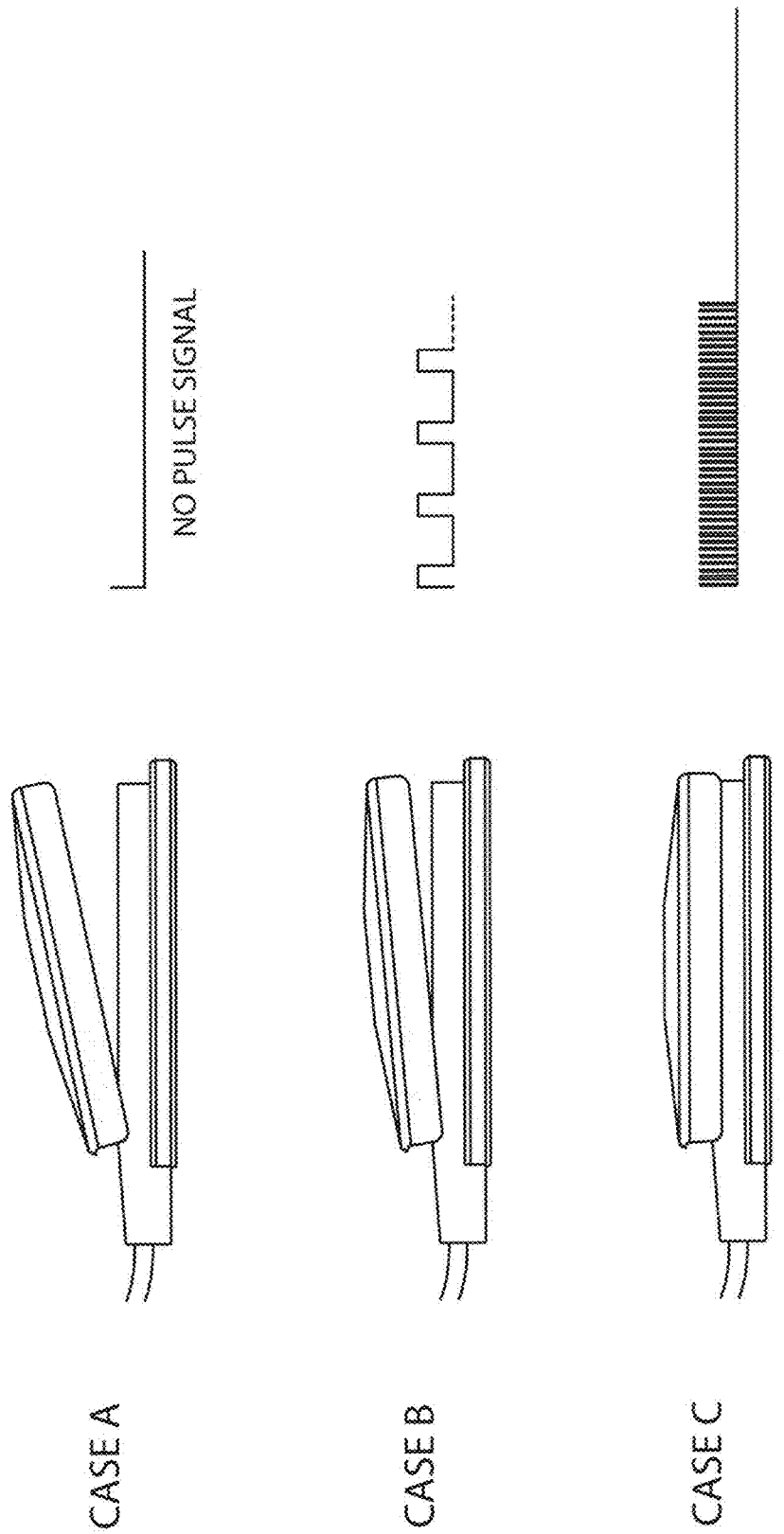

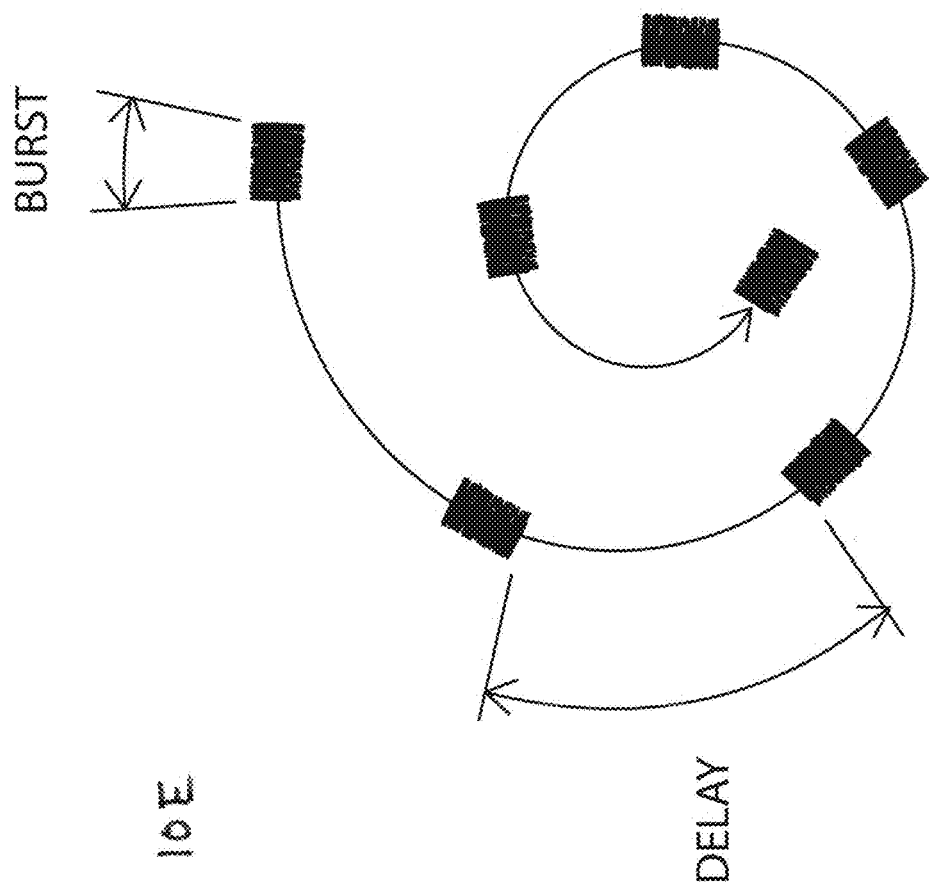

DENTAL LASER APPARATUS AND METHOD OF USE WITH INTERCHANGEABLE HAND PIECE AND VARIABLE FOOT PEDAL

CROSS REFERENCE TO RELATED APPLICATIONS

This application claims benefit of priority to U.S. Provisional Patent Application No. 61/761,020, entitled "Dental Laser Apparatus and Method of Use with Interchangeable Hand Piece and Variable Foot Pedal," filed on Feb. 5, 2013; U.S. Provisional Patent Application No. 61/793,006, entitled "Dental Laser Apparatus and Method of Use with Interchangeable Hand Piece and Variable Switch," filed on Mar. 15, 2013; and U.S. Provisional Patent Application No. 61/909,929, entitled "Rotationally Orientable Dental Laser Hand Piece," filed on Nov. 27, 2013, the disclosures of each of which is incorporated herein by reference in its entirety.

FIELD OF THE INVENTION

The present invention relates to laser treatment systems and, more specifically, to dental laser treatment systems utilizing detachable hand pieces.

BACKGROUND

Dental laser systems typically use a hand piece for directing laser light or cooling fluids to an oral treatment area. Lasers can be useful in several hard and soft tissue dental procedures, including: removing decay, cutting, drilling or shaping hard tissue, and removing or cutting soft tissue.

A tooth has three layers. The outermost layer is the enamel which is the hardest and forms a protective layer for the rest of the tooth. The middle and bulk of the tooth is made up of the dentin, and the innermost layer is the pulp. The enamel and dentin are similar in composition and are roughly 85% mineral, carbonated hydroxyapatite, while the pulp contains vessels and nerves which are sensitive to pressure and temperature. Hydroxyapatite absorbs laser light in the 9.3-9.6 µm wavelength range more efficiently than radiation in any other wavelength range. Absorption of the laser energy can increase the temperature of any of the layers of the tooth. In cutting, contouring, or conditioning the enamel and dentin, it is beneficial to account for the pulp's temperature sensitivity because a rise in temperature of about 5.5° C. can lead to permanent damage of the tooth's pulp.

Lasers have been found to be useful in the removal of dental material without the use of local anesthetic similar to that required when the procedure is performed with a conventional drill. Moreover, lasers do not make the noises and vibrations that are associated with dental drills. For these reasons it has been the hope of many in the dental industry that lasers may replace the drill and alleviate, at least to some extent, the anxiety and fear from dental treatment.

Unlike dental drills a dental laser is an end cutting device, i.e., material is generally removed from the end of a focused laser beam. In contrast, a drill is side cutting device, i.e., the material is milled away by the side of the burr. The general inability of a laser device to side cut similarly as a drill can be a limitation in the use thereof. Therefore, an agile hand piece may be useful to make the many dental surfaces and locations accessible for laser treatment in order to make the use of laser technology in dentistry practical. Difficulty often arises in reaching the different treatment areas with only one hand piece tip or a hand piece that cannot fully rotate. During treatment, a required amount of coolant must also be delivered to a selected target area so as to avoid an excessive rise in the temperature thereof.

The effectiveness of the laser in treatment can depend on a number of variables. For example, the frequency and pulse width of the laser pulses typically determine the average power of the laser; a controlled volume of the flow of a coolant to the treatment area can prevent over heating of the pulpal chamber and/or melting of enamel and may also minimize power losses from attenuation of the delivered laser energy by absorption in the coolant. Setting these variables to suitable values and controlling them throughout a procedure can be beneficial to dental treatment.

Conventional dental treatment systems, such as pneumatic and electric drills, often include a foot pedal using which an operator can control the rotational velocity and/or power of the burr, allowing material removal rates to be varied throughout the procedure without needing to pause the procedure to adjust power settings. In laser-based dental systems a foot pedal may be used to actuate the firing of the laser as well as to actuate or stop the flow of the coolant. A desired laser power is usually first set by the operator, and then the laser can be fired by depressing the foot pedal or turned off by releasing the pedal. If any parameter of the treatment is to be changed, the procedure is typically suspended, the operator may adjust one or more system parameters, and may then resume the procedure. A pulse rate of the laser is one parameter that can be controlled to control the amount of laser energy delivered to the treatment area. Controlling only the pulse rate, however, is not effective in many treatment procedures.

Various presently used laser-based dental treatment systems have several additional disadvantages. For example, these systems generally require a dedicated hand piece, and do not support the use of interchangeable hand pieces. Various hand pieces commonly used do not simultaneously deliver both laser pulses and coolant. Moreover, the hand pieces are typically not rotatable so that an operator can direct laser energy to any selected location of the tooth or gum, without causing significant discomfort to a patient. Therefore, improved laser-based treatment systems and methods are needed.

SUMMARY

Various embodiments of the present invention are directed to a dental laser apparatus that satisfies one or more of the needs identified above. This is achieved, in part, by providing an apparatus having an affixable hand piece that can simultaneously deliver laser pulses and coolant to a treatment region. The handpiece may be rotatably affixed to a main chamber. A groove and sealing mechanism facilitates delivery of the fluids of a coolant, e.g., air and water, as the handpiece is rotated. Thus, the user (e.g., a physician) can rotate the handpiece to direct laser energy to a selected location in the patient's mouth, without interrupting the treatment.

The handpiece may include circuitry that stores information about the features of the handpiece such as tip angle, length of the handpiece, etc. The main chamber to which the handpiece is to be affixed can read the stored information and automatically adjust parameters of the laser delivery system, such as angles of mirrors, focal length of a lens, etc. This allows the user to switch handpieces as necessary, without having to manually reconfigure the laser delivery system.

An optional foot pedal of the dental laser apparatus may vary characteristics of the sequence of laser pulses, such as the pulse rate, pulse width, energy per pulse, etc. As a pulse-sequence parameter changes in response to movement of the foot pedal, the galvos in an optical system in the main chamber may be adjusted according to the selected pulse-sequence parameters. This allows the user to finely control the cutting procedure, by adjusting the delivery of laser energy as needed.

Accordingly, in one aspect, an apparatus for directing a laser beam to a dental treatment area includes a main chamber and a hand piece affixable to the main chamber. The main chamber includes an optical subsystem and a primary fluid supply subsystem. The optical system is adapted to direct a laser beam to a dental treatment area, and the primary fluid supply subsystem is adapted to direct fluid to the treatment area. The hand piece includes a mating optical subsystem and a mating secondary fluid supply subsystem, such that upon affixing the hand piece to the main chamber, the secondary fluid supply subsystem forms a fluidic communication with the primary fluid supply subsystem, for providing a coolant to the dental treatment area simultaneously with the laser beam. The mating optical subsystem aligns with the optical subsystem for providing the laser beam to the dental treatment area.

In some embodiments, the hand piece is rotatably affixable to the main chamber. The primary fluid supply subsystem and the secondary fluid subsystem include an annular groove set and a corresponding radial port such that a fluidic communication is maintained when the hand piece is rotated relative to the main chamber.

The primary fluid supply subsystem may include a primary water channel and a primary air channel. The secondary fluid supply subsystem may include a corresponding secondary water channel and a corresponding secondary air channel and, correspondingly, the groove set may include first and second annular grooves such that the primary and secondary water channels form a fluidic communication via the first groove and the primary and secondary air channels form a fluidic communication via the second groove. The apparatus may also include a sealing mechanism associated with the primary and secondary fluid supply subsystems. The sealing mechanism may include at least one O ring.

In another aspect, an apparatus for directing a laser beam to a dental treatment area includes a main chamber that includes an optical subsystem. The apparatus also includes a hand piece affixable to the main chamber. The hand piece includes circuitry that can store information relating to a feature of the hand piece. The feature can be a tip at a certain angle, e.g., an about 90 degree tip, a contra-angle, 105 degree tip, etc. In some embodiments, the information encoded in the circuitry includes one or more of a length of the hand piece, a diameter of the hand piece, an angle of the tip, and a standoff distance of the tip from the dental treatment area.

In various embodiments, the hand piece can be rotatably affixable to the main chamber. The apparatus may include a mechanism for preventing the hand piece from rotating. The apparatus may also include an interface to establish an electrical communication between the circuitry in the hand piece and a processor, for extracting by the processor the encoded information. Alternatively, the apparatus may include a slip ring to establish an electrical communication between the circuitry in the hand piece and a processor, for extracting by the processor the encoded information. In some embodiments, the apparatus may include an RFID transponder to establish communication between the circuitry in the hand piece and a processor, for extracting by the processor the encoded information.

In another aspect, an alignment attachment affixable to hand piece used for directing a laser beam to a dental treatment area includes a target component and a standoff fixture affixable to a tip of the hand piece. The standoff fixture may dispose the target component substantially at a focal point of a laser beam emerging from the tip. The target component may include a plastic disc.

In one aspect, a foot pedal for controlling a laser-based dental treatment system includes an upper surface adapted for contact by a user's foot for controlling power of a laser beam used for dental treatment. The foot pedal may be adapted for adjusting a laser pulse repetition rate and/or laser energy per pulse. Alternatively or in addition, the foot pedal may be adapted for adjusting a galvo rate.

In one aspect, a method is provided for directing a laser beam to a dental treatment area using a laser-based treatment system having a main chamber and a removable hand piece having a tip. The method includes retrieving information related to the tip from circuitry located within the hand piece after the hand piece is affixed to the main chamber. The method also includes adjusting a position of a mirror of a primary optical subsystem within the main chamber based on, at least in part, the retrieved information, such that a laser beam passing through the primary optical subsystem and a secondary optical subsystem within the tip is directed to a selected spot of a dental treatment area.

In another aspect, a method of directing a laser beam to a dental treatment area using a laser-based treatment system includes delivering, via a movable mirror, a series of bursts of laser pulses. Each burst may include an ON interval followed by an OFF interval. Laser pulses may be directed to the dental treatment area during the ON interval and substantially no laser pulses may be directed to the dental treatment area during the OFF interval. The method also includes adjusting a position of the mirror so as to direct the laser pulses: (i) to a first location within the treatment area during a first burst of the series of bursts, and (ii) to a second location within the treatment area during a second burst of the series of bursts.

The method may further include selecting one or more of a duration of the ON interval, a duration of the OFF interval, and a duration of the burst using a foot pedal. In some embodiments, the method includes configuring a foot pedal to select a duration of one or more of the ON interval, the OFF interval, and the burst.

In one aspect, a method of directing a laser beam to a dental treatment area using a laser-based treatment system includes delivering a series of bursts of laser beam pulses. The laser beam may include a wavelength in a range of about 9 µm up to about 11.5 µm. Each burst may include an ON interval followed by an OFF interval, and the laser pulses may be directed to the dental treatment area during the ON interval and substantially no laser pulses may be directed to the dental treatment area during the OFF interval.

In some embodiments, the method further includes adjusting a position of a movable mirror so as to direct the laser pulses: (i) to a first location within the treatment area during a first burst of the series of bursts, and (ii) to a second location within the treatment area during a second burst of the series of bursts. In some embodiments, the method includes generating the laser beam using a mid-pressure, i.e., about 260 to 600 Torr, CO2 laser.

According to a one aspect, an apparatus for directing a laser beam to a dental treatment area includes a housing forming a main chamber. The apparatus include a main optical subsystem and a primary fluid supply subsystem, adapted to direct a laser beam and fluid to a dental treatment area. A removable hand piece is affixable to the main chamber, the hand piece including a mating optical subsystem and a mating secondary fluid supply subsystem. The hand piece is rotatable about an optical axis within the hand piece. A lock maintains a selectable angular orientation of the hand piece relative to the main chamber when engaged and permits the hand piece to rotate about the optical axis thereof, when disengaged. In various embodiments, the lock is in the form of a clamp.

When the hand piece is affixed to the main chamber, the secondary fluid supply subsystem forms a fluidic communication with the primary fluid supply subsystem, for providing a coolant to the dental treatment area simultaneously with the laser beam. In some embodiments, the primary fluid supply subsystem and the secondary fluid subsystem include an annular groove set and a corresponding radial port, such that fluidic communication is maintained when the hand piece is rotated relative to the main chamber. The apparatus optionally includes a sealing mechanism associated with the primary and secondary fluid supply subsystems, for example at least one O ring.

According to another aspect of the invention, certain embodiments are defined by an apparatus for directing a laser beam to a dental treatment area, the apparatus including a housing forming a main chamber for a main optical subsystem and a primary fluid supply subsystem, the apparatus adapted to direct a laser beam and fluid to a dental treatment area. A hand piece is affixable to the main chamber, the hand piece including a mating optical subsystem and a mating secondary fluid supply subsystem. The hand piece is rotatable about an optical axis within the hand piece. A lock maintains a selectable angular orientation of the hand piece relative to the main chamber when engaged and permits the hand piece to rotate about the optical axis thereof, when disengaged. An angular measurement sensor is provided, for measuring a selected angular orientation of the hand piece relative to the main chamber. A controller is adapted to adjust the main optical subsystem based, at least in part, on the selected angular orientation, so as to align the main optical subsystem with the mating optical subsystem.

In certain embodiments, the controller is adapted to adjust the main optical subsystem such that upon engaging the lock, a main optical axis of the laser beam, within the main chamber, is substantially collinear with the optical axis of the hand piece. According to various embodiments, the main optical subsystem includes at least one mirror adjustable by a motor and the controller is adapted to control the motor to adjust an initial position of the at least one mirror. Alternatively or additionally, the controller includes at least one of a function-based calculator, the function specifying an adjustment to the main optical subsystem according to the selected angular orientation, and a look-up table specifying an adjustment to the main optical subsystem according to the selected angular orientation.

According to another aspect of the invention, various methods associated with the manufacture and use of the aforementioned apparatus, structures and systems are contemplated and are to be considered within the scope of the invention describe herein.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals generally refer to the same or similar elements. In different drawings, the same or similar elements may be referenced using different reference numerals. The drawings are not necessarily to scale, emphasis instead being placed upon illustrating aspects of the invention. In the drawings:

FIG. 2A depicts a cross-section of a hand piece having a right-angle tip and a main chamber, according to one embodiment;

FIG. 2B depicts a cross-section of a hand piece having a contra-angle tip, according to one embodiment;

FIGS. 3B and 3C illustrate coupling of the hand piece and the main chamber depicted in FIG. 3A;

FIG. 4 depicts a cross section a hand piece including a waveguide, according to one embodiment;

FIGS. 5B-5D schematically illustrate various embodiments of circuitry for the alignment of a hand piece and the main chamber;

FIGS. 6A-6C depict components for testing of the alignment, according to various embodiments;

FIGS. 7A and 7B depict cross-sections of a hand piece and a main chamber, according to one embodiment;

FIG. 7C depict exposed components of the hand piece and the main chamber depicted in FIGS. 7A and 7B;

FIG. 9B schematically illustrates control of a pulsed laser using a foot pedal, according to one embodiment;

FIGS. 10C-10E schematically illustrate movements of a laser beam and corresponding delivery of energy to a treatment area, according to various embodiments.

DETAILED DESCRIPTION

Laser-Based Dental Treatment System

Figure 1A:
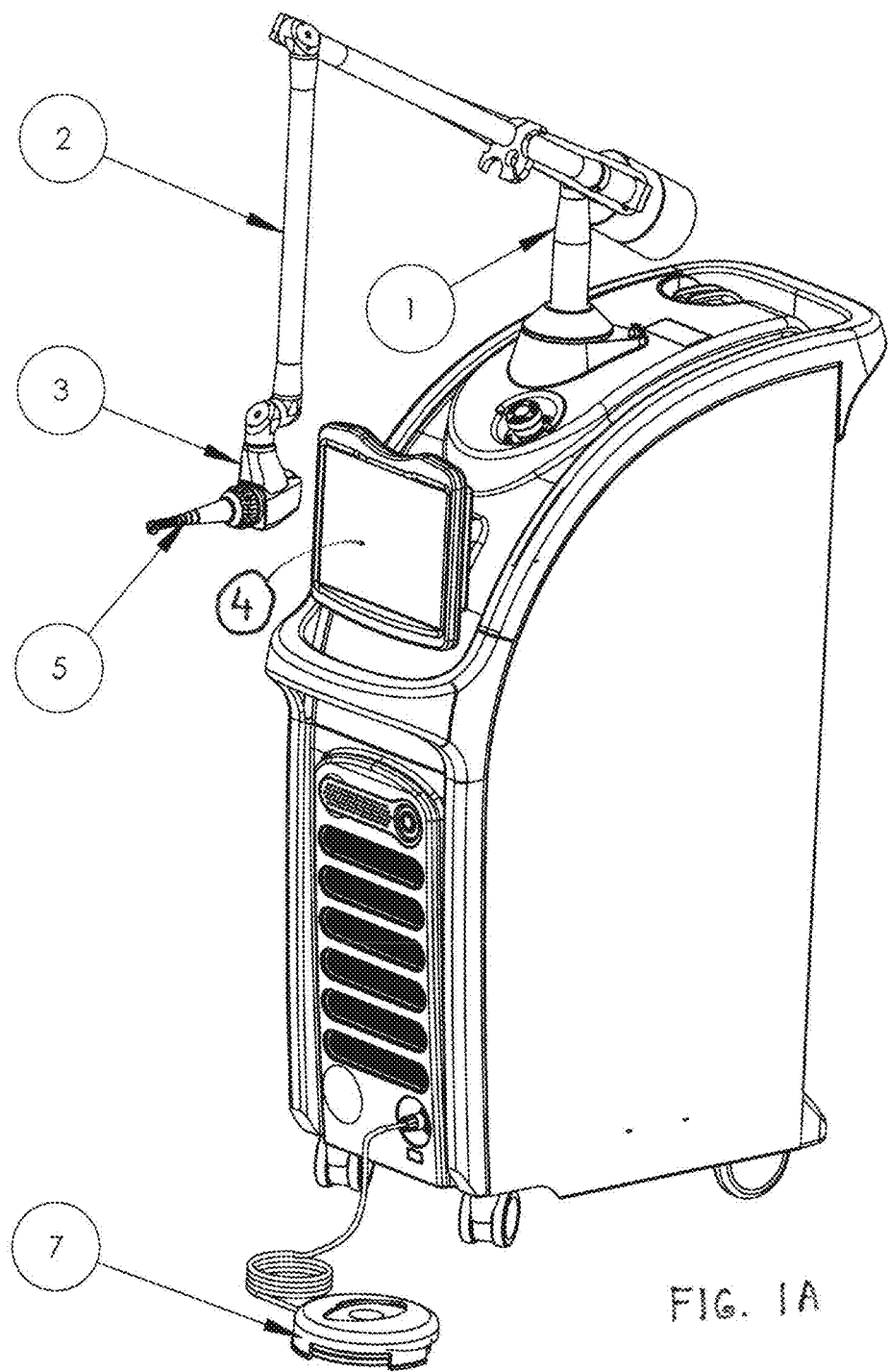
FIG. 1A depicts various components of an embodiment of a dental laser system.

With reference to FIG. 1A, in an exemplary laser-treatment apparatus 100, a laser beam from a laser source is directed into an articulating arm launch 1. The beam is further directed into an articulated arm 2, and exits therefrom through an end opposite the launch 1. A dental laser system 3 includes an interchangeable hand piece 5. A foot pedal 7 can control the dental laser system 3. It should be understood that the foot pedal 7 is illustrative only and that the control of one or more parameters of a dental laser system, as described below, can be achieved using any suitable switch such as a mouse, keyboard, joy stick, touch screen panel, a slider switch, etc.

Figure 1B:
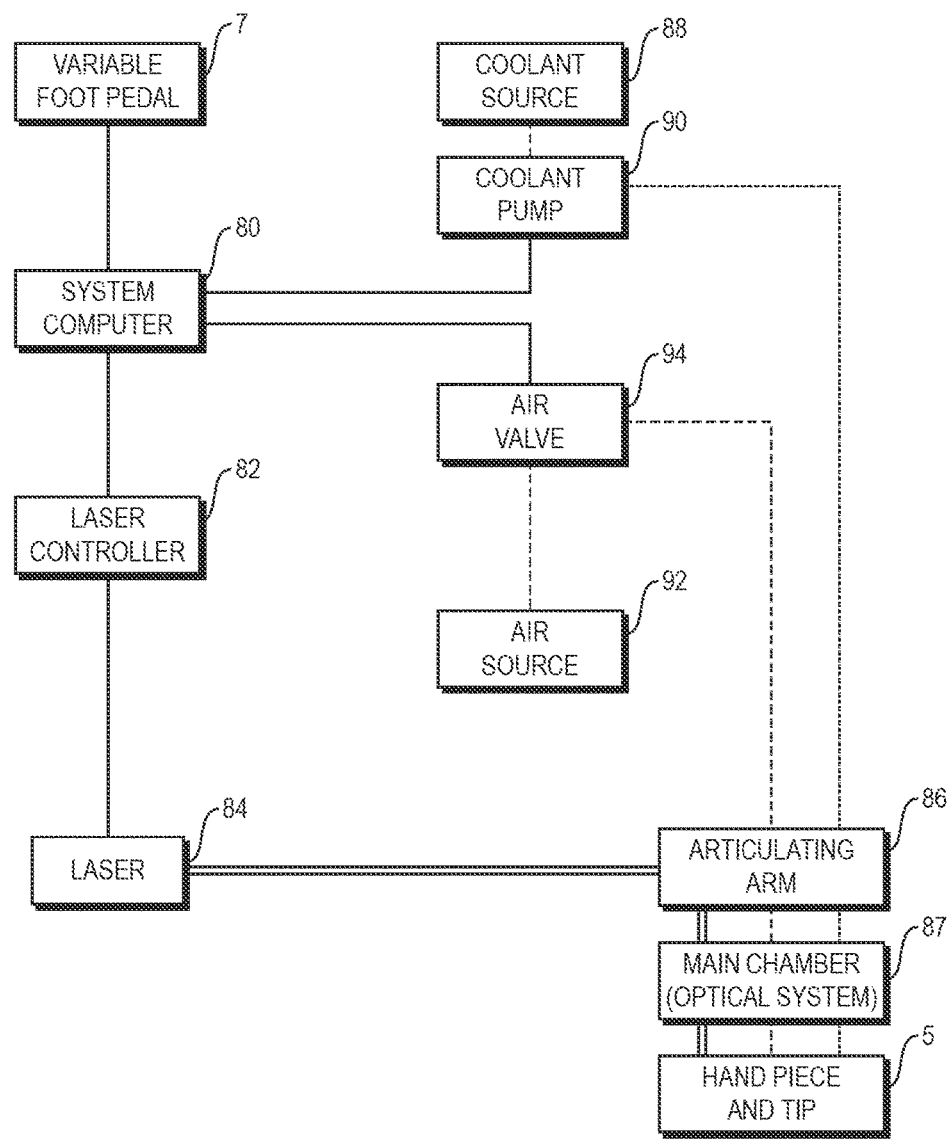
FIG. 1B schematically depicts various components of an embodiment of a dental laser system.

With reference to FIG. 1B, the pressure applied to the foot pedal 7 can be varied, for example, to control a computer 80, which in turn can control a laser controller 82, so as to control the operation of a laser source 84. Using the foot pedal 7 (or any switch, in general), the laser source 84 may be turned on/off, and/or other system parameters such as the pulsing of the laser beam, intensity thereof, rate of flow and/or pressure of a coolant, etc., may be controlled. The laser beam generally passes through an optical system 87 within an articulating arm 86 to a main chamber. Via another optical system within the main chamber, the laser beam is directed to a tip of a hand piece 5. A coolant from a coolant source 88 may be supplied using a computer-controlled coolant pump 90 to the hand piece 5 via the articulating arm 86. Pressurized air from an air source 92 may also be supplied using a computer-controlled valve 94 to the hand piece via the articulating arm 86. The pressurized air may be used in combination with the coolant to generate a cooling mist and/or may be used to protect various components located in the hand piece 5.

Freely Rotatable Hand Pieces

With reference to FIG. 2A, a hand piece 205a includes an about 90° turning optic 201 that can redirect the laser beam from an axis 204a to another axis 204b. The water and/or air conduits 202 pass through the hand-piece 205a and exit via a cutting insert 219. The air and water mist can flow out of the cutting insert 219 via the misting orifices 220. The cutting insert 219 is mounted within an about 90° tip 221 which can be attached to the hand piece 205a.

A laser beam typically enters a main chamber/housing 203 through a top opening thereof and passes through a focusing optic 211. The laser beam then reflects off the two mirrors 213a, 213b, controlled via corresponding galvos/ servos 212a, 212b, and propagates substantially along the optical axis 204a. The laser beam then reflects off the about 90° turning mirror 201, and is directed substantially along the axis 204b.

Illumination light produced by diodes 215 disposed on an illumination board 214 passes through a light funnel 216 towards the about 90° turning mirror 201. A rotating drum 206 of the hand piece 205a has three grooves 224. Each groove is fed via a corresponding conduit 222; two air conduits and one water conduit. The grooves 224 are sealed with four O-rings 217. The rotating drum 206 is held substantially in place using bearings 218, but the bearings permit the drum and, hence, the hand piece 205a to freely rotate about the optical axis 204a. Thus, an operator can conveniently orient the tip on the hand piece to direct the laser beam to a selected area of treatment. A plastic housing 210 substantially covers the whole assembly for dust sealing. A knob 208 (also called a locking ring) interfacing with a ramp 209 allows the hand-piece 205 to be easily removed and changed while substantially mainlining an optical alignment, i.e., the laser beam reflected by the mirrors 213a, 213b in their rest position is directed substantially along the optical axis 204a.

The interchangeable hand piece 205a is attached using a locking ring 208 to a rotating drum 206 which is attached to the main chamber 203 that provides the laser beam from the source to the hand piece 205a. The rotating drum 206 may be held stationary to allow for rotation of the locking ring 208 relative to the drum 206. This can be achieved using a plunger that enters an axial opening in the drum 206 when depressed to prevent rotation of the drum 206 or by using a circumferential grip that an operator may hold to substantially prevent the drum 205 from rotating. Once the locking ring 208 locks and thus attaches the hand piece 205a to the main chamber 203, the plunger may be released, allowing the drum and the hand piece 205a to rotate freely within a housing using the bearings 218.

The assembly of the grooves 224 around the circumference of the drum 206, axial openings in the drum, radial openings in the surface of the main chamber over the grooves, and the O-rings 217 creates a fluidic communication between the feed conduits 222 and the corresponding air and water conduits 202 even when the hand piece 205a freely rotates about the optical axis 204a. This allows delivery of fluids from the main chamber to the tip 221 of the hand piece 205a

When the fluids (e.g., coolant fluids such as air and water) reach the hand piece tip 221 these fluids can be mixed together in a mixing channel and may then be discharged through an orifice 220 of a selected shape and size to create a cooling mist. The cooling mist can be directed to the treatment area to cool and prevent the tooth from becoming heated to an unsafe temperature. The direction of the misting orifices can be selected to focus the mist at or near the center of the area being treated by the laser. A mist that is not focused at or near the laser treatment area or that is insufficient, can cause melting of the tooth enamel, which can significantly interfere with the treatment of hard tissue. The groove-O-ring assembly, enables the fluidic communications and delivery of fluids to the tip of the hand piece, so as to enable the creation and delivery of a suitable cooling mist.

A separate air flow can also be provided to the tip of a hand piece in a similar manner as the misting fluids to create a jet of air. The air jet may be formed across the laser beam and may exit through an enlarged outlet 219 to provide a laminar flow air knife barrier. Alternatively or in addition, the air jet may be formed over the turning mirror 201 creating an air sheath thereover in order to redirect any debris away from the turning mirror.

The air jet can minimize or eliminate any debris such as coolant splashing from the treatment surface or ablated material from the treatment area that can enter the tip 221 through the opening thereof. Such debris can contaminate the turning mirror 201 used to direct the focused laser beam to the treatment area, and thus affect the treatment in an undesirable manner.

With reference to FIG. 2B, another interchangeable hand piece 205b has a tip angle of about 105°. This contra-angle hand piece typically allows for treatment of dental areas at an angle other than about 90°. Air and water conduits 202 feed fluids into the hand-piece tip 221, to form a mist to be directed to a treatment area via the misting orifices 220. The contra-angle tip 221 is at an angle of about 105° relative to the optical axis 204b, and the contra-angle turning mirror 207 is at an angle of about 7.5° relative to a turning mirror of a right-angle hand piece tip. For example, a right angle tip turning mirror may be disposed at an angle of about 45° relative to the optical axis of the hand piece, while a contra-angle tip turning mirror may be disposed at an angle of about 52.5° relative to the optical axis. The hand piece 205b also includes an air window 219 through which an air jet across an opening of the tip 221 may exit. The same fluidic communication system in the main chamber 230 that may be used with the hand piece 205a can be used with this removable hand piece 205b as well. The angle of the hand piece tip may be encoded in an associated recognition chip and may be read by the internal computer, allowing for necessary adjustments to optical system and/or beam scanning patterns without significant user intervention.

Figure 3A:
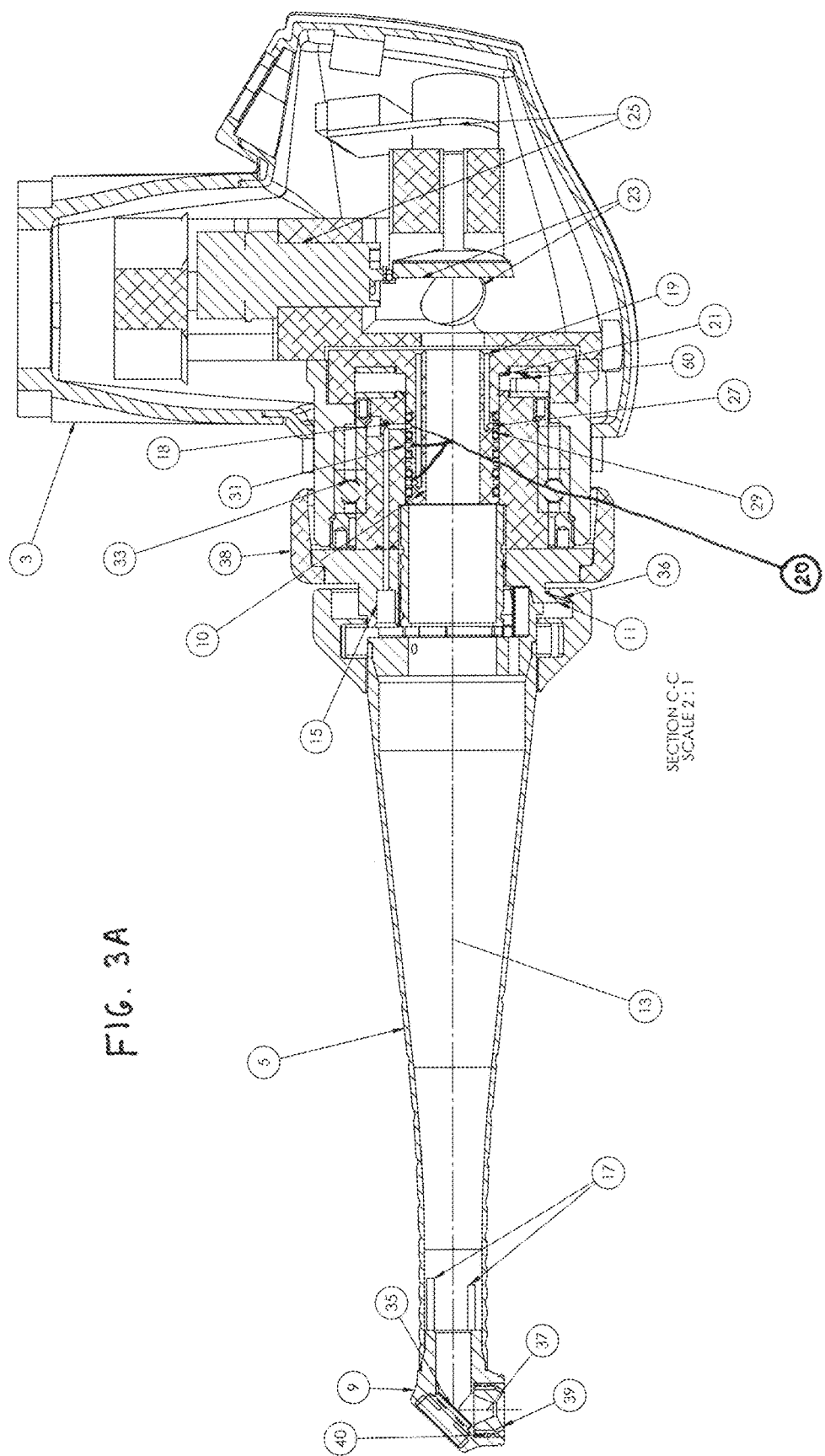
FIG. 3A depicts a cross-section of a hand piece having a right-angle tip and a main chamber, according to another embodiment.

With reference to FIG. 3A, a right-angle (about 90°) hand piece tip 9 is attached to an interchangeable hand piece 5. The dental laser system 3 includes a main chamber 10 through which the laser is directed after exiting the articulating arm. The hand piece 5 is connected to the main chamber 10 using a coupling 11. The hand piece 5 and main chamber 10 both include a first optical axis 13. Coupling 11 allows for attachment of the hand piece 5 to the main chamber 10 such that the axis 13 of the hand piece and the axis 13 within the main chamber 10 are substantially collinear, thereby aligning the interchangeable hand piece 5 with the main chamber 10. This generally allows the laser beam to be directed through the hand piece towards a specified target region.

The laser beam is directed through the main chamber 10 toward the interchangeable hand piece 5 using one or more adjustable mirrors 23. Galvanometers 25 (servomechanisms, in general) are attached to the mirrors 23 to allow for angular movement of the mirrors and electronically controlled beam guidance. The laser beam can have a wavelength in a range of about 9 µm to about 11.5 µm, and may be obtained using a mid-pressure laser source. The beam may be generated using a $CO_2$ laser.

One or more primary fluid ports 19 located within a primary manifold 21 in the main chamber 10 are in fluidic communication with one or more fluid sources (not shown). Fluids such as a liquid coolant and air may flow from their respective sources to the respective primary fluid ports 19. The coupling 11 includes one or more secondary fluid ports 15 each of which is in fluidic communication with at least one of secondary tubes 17 (partially shown) in the interchangeable hand piece 5, thus allowing for fluidic communication from one or more primary fluid sources to the hand piece tip 9. For example, in one embodiment coolant and air are delivered to a mist nozzle 39 including a mixing chamber 40 where the fluids are combined and jetted out forming an atomized mist of coolant spray.

To this end, one or more annular grooves 27 are formed in the main chamber 10. The grooves are generally concentric relative to a first optical axis 13 and are contained by one or more seals 29. The sealing can be provided, for example, by two O rings 29 on two sides of a groove, such as the groove 27. In one embodiment, the groves 27 are formed in the top surface of the primary manifold 21 of the main chamber 10. A secondary manifold 31 can rotate over the grooves 27. The secondary manifold 31 contains cross drilled openings 20. Each opening 20 is coupled to a corresponding outlet 18, and is also associated with one of the grooves 27. This allows for fluidic communication between the grooves 27 and the corresponding secondary fluidic outlets 18.

The secondary fluid outlets 18 are coupled to the corresponding secondary fluidic ports 15 in the handpiece coupling 11. As the hand piece 5 is rotated around the optical axis 13, the secondary manifold 31 can also rotate over the primary manifold 21. The secondary fluid outlet 18 may maintain a fluidic communication with the groove 27 via the aperture 20 during the rotation. Thus, a fluidic communication can be maintained between the primary ports 19, the corresponding secondary outlets 18, the corresponding secondary ports 15, and the corresponding secondary tubes 17, as the hand piece is rotated about the axis 13.

With reference to FIG. 3B, a first primary fluid port 19a is in fluidic communication with a first annular groove 27a located farthest to the right in the main chamber 30. The first annular groove 27a is also in fluidic communication with a first secondary fluid port 15a on the interchangeable hand piece coupling 11, via an opening 20a and an outlet 18a, as described above. The secondary fluid port 15a can be seen in one rotational orientation of the hand piece 5 relative to the optical axis 13, as seen in the cross section AA. This arrangement allows for sealed fluidic communication between first primary fluid port 19a and a corresponding first secondary fluid port 15a through complete rotation of the coupled hand piece 5 about the optical axis 13.

With reference to FIG. 3C, a second primary fluid port 19b is in fluidic communication with a second annular groove 27b, located near the far left end of the main chamber 30. The second annular groove 27b is in fluidic communication with a second secondary fluid port 15b, which can be seen in a different rotational orientation of the hand piece 5 relative to the optical axis 13, as depicted in cross-section BB. The second primary fluid port 19b and second secondary fluid port 15b can maintain sealed fluidic communication via an opening 20b and an outlet 18b through a full rotation via the second annular groove 27b that runs entirely around the circumference of the primary manifold 21.

Figure 3D:
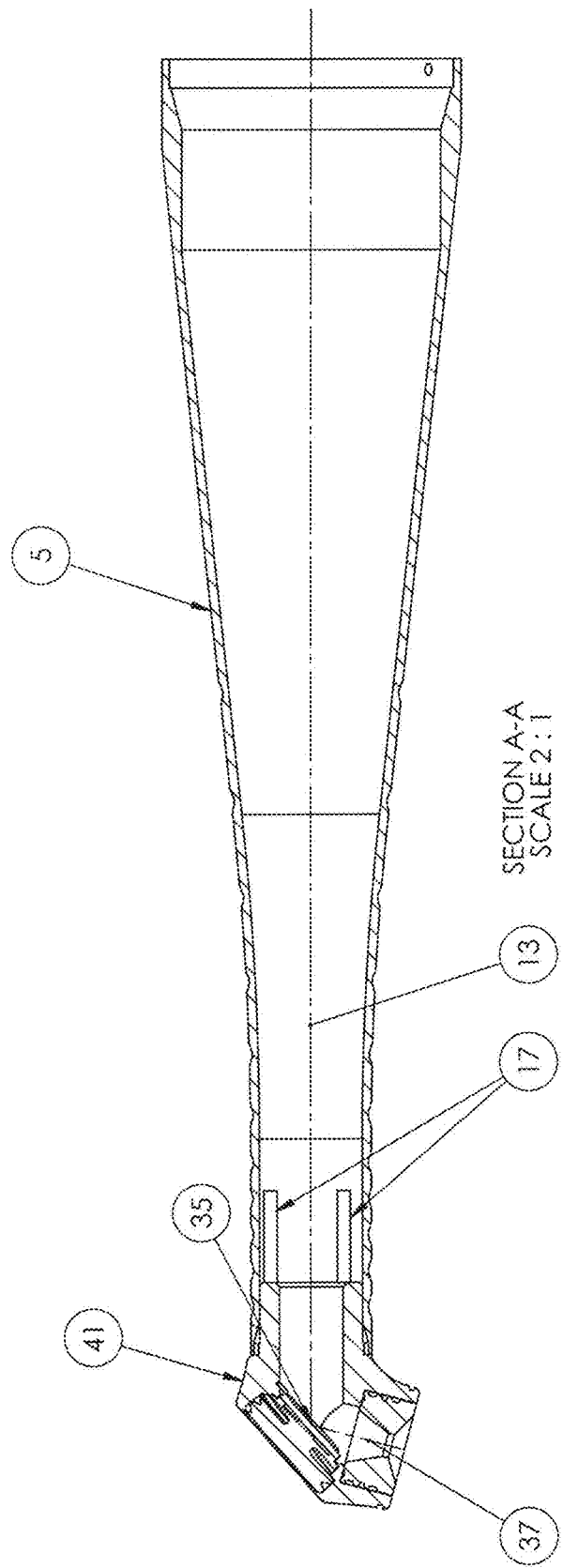
FIG. 3D depicts a cross-section of a hand piece having a contra-angle tip, according to one embodiment.

Referring again to FIG. 3A, the rotation of the hand piece 5 and the coupling 11 is facilitated by bearings 33. The interchangeable hand piece 5 mates with the coupling 11 and is rotatably affixed to the main chamber 10. In one embodiment, the interchangeable hand piece 5 is affixed to the coupling through a bayonet locking feature 36. The rotation of the hand piece 5 can be prevented using a grip 38. In one embodiment of the interchangeable hand piece 5, a turning mirror 35 directs the incident laser beam from first optical axis 13 to the treatment area along a second optical axis 37. In the embodiment depicted in FIG. 3A the angle between the first and second optical axis is about 90°. In another embodiment depicted in FIG. 3D this angle is about 105°. With reference to FIG. 3D, a contra-angle hand piece tip 41 produces the about 105° angle between the optical axes 13, 37. These two angles (i.e., about 90° and about 105°) are illustrative only. Hand piece tip angles within the range of 75° to 125° may be used.

Figure 3E:
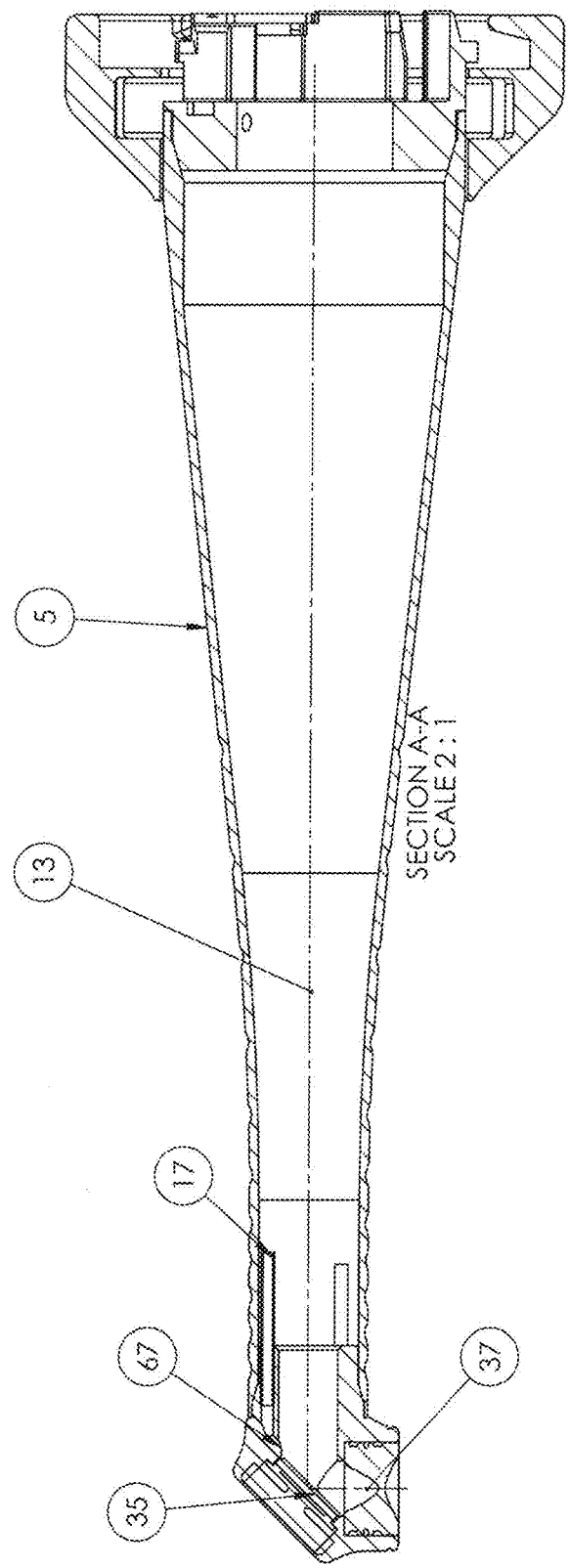
FIG. 3E depicts a cross-section of a hand piece that includes a nozzle for a jet steam across a turning optic.

With reference to FIG. 3E, within the interchangeable hand piece 5 a turning mirror 35 directs the laser beam incident from the optical axis 13 to the treatment area along a second optical axis 37. During dental operation coolant and/or debris may enter through an opening in the tip around the axis 37, and may settle on the reflective surface of the mirror 35, thereby affecting the reflectivity of the mirror. To prevent or at least mitigate such contamination, a fluid (typically compressed air) flow that is substantially parallel to and over the turning mirror 35 can be formed using a nozzle 67 to provide a protective barrier over the turning mirror 35. A typical air pressure supplied by the nozzle 67 is about 40 psi. In general, the air pressure can vary from about 10 psi up to about 100 psi. The fluid flow or jet can prevent large particles of ablated material from fusing to the turning mirror 35.

In some embodiments, a hand piece can include a straight hollow wave guide or fiber. With reference to FIG. 4, a hollow wave guide 43 is affixed to a threaded hub 45 and the two are threaded into a receiver 47 on an interchangeable hand piece 5 such that the hollow wave guide 43 is substantially concentric with the primary optical axis 13. The hollow wave guide 43 and threaded hub 45 may be replaced in between treatments. The hollow wave guide 43 may also be bent to deliver laser energy to areas or regions that cannot be conveniently treated using a nonflexible hand piece or using a conventional burr.

Alignment of Hand Pieces

The interchangeable hand pieces may contain an encoded chip that contains information specific to the individual interchangeable hand piece. When the hand piece is attached to the main chamber an electrical connection between the chip and an internal computer in the dental laser system may allow the computer to read of the encoded material located on the chip. The dental system can be configured such that it can be operated only if the system computer recognizes the attached hand piece by retrieving encoded information on a chip thereon. A chip on a hand pieces may include certain defining characteristics of the hand piece including the length of the hand piece, location of the central axis thereof, a default procedure associated with the hand piece, fluid pressure and flow requirements, laser power limits, and available scanable area. Using this information the capabilities of an attached interchangeable hand piece may be identified, and the system defaults may be set.

As one hand piece is replaced with another, small differences in alignment between in individual interchangeable hand pieces can occur. This can result in a variation in the location of the center of the turning mirror 35 within a hand piece or the center of the hollow wave guide 43, from one interchangeable hand piece to another. In other words, an optical axis within a hand piece may not be substantially collinear with the corresponding optical axis in the main chamber 30. Consequently, when one hand piece is replaced with another, the laser beam may not be directed to a target region. Such misalignment can be eliminated or at least minimized by recognizing each hand piece as it is attached to the main chamber and, using information about the attached hand piece, adjusting the optical system in the main chamber such that the optical axes within the main chamber and the attached hand piece are substantially collinear.

Figure 5A:
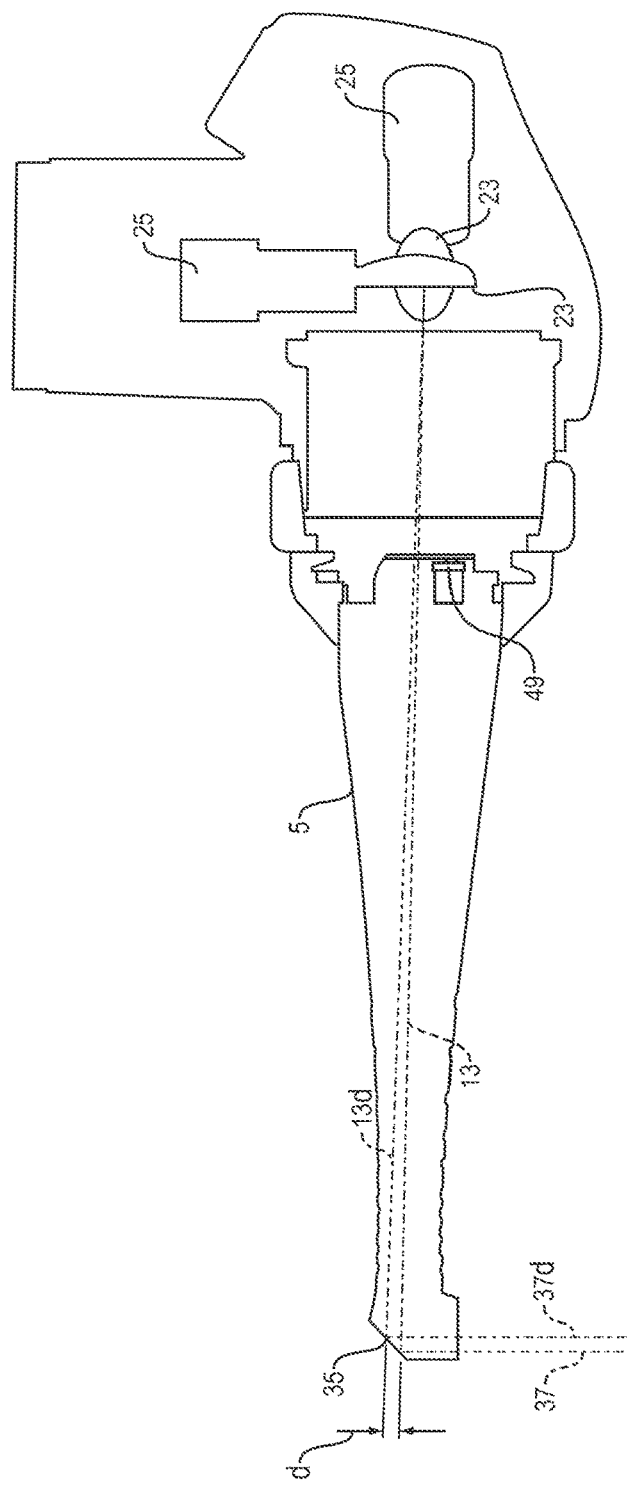
FIG. 5A schematically illustrates alignment of a hand piece and the main chamber, according to one embodiment.

To this end, as depicted in FIG. 5, different types of hand pieces (e.g., having a tip angle of about 90°, having a contra angle tip, a hollow wave guide or fiber, etc.) can be recognized by the laser system using a one wire recognition board 49 attached to each interchangeable hand piece 5. The one wire recognition board 49 may be grounded to the chassis of the laser system and may require only a single electrical connection to the board to form the necessary electrical circuit that can recognize characteristics of the hand piece 5. The single connection can allow rotation of the hand piece relative to the main chamber.

The actual location of the turning mirror or of the center of the mirror or the hollow wave guide of each individual hand piece may be encoded on the one-wire recognition board 49. When the interchangeable hand piece 5 is connected to the laser system 3 the encoding may read by the laser system allowing the galvanometers/servos to redirect the beam such that the first optical axis 13 (i.e., the optical axis within the main chamber 30) is substantially aligned with the center of the attached interchangeable hand piece 5.

To illustrate, there may be a small deviation d in the location of the center of the turning mirror 35 in one hand piece and the first optical axis 13. The deviation d may be encoded on the one wire recognition board 49 of the interchangeable hand piece 5 having that deviation with respect to the location of the center of the turning mirror in a reference hand piece. When the hand piece 5 is attached to the system 3, the deviation d can be read into the dental laser system 3 and the galvanometers/servos 25 readjust the initial angular position of the mirrors 23. This can re-orient the first optical axis 13, to account for the deviation, to an adjusted first optical axis 13d. This adjustment can cause a further adjustment of the second optical axis 37, to an adjusted second optical axis 37d, which may be directed to the specified target area/region. Other parameters that may be encoded on the recognition board, alternatively or in addition, include: the number of times of the hand piece has been attached to the laser system, and the serial number of the individual interchangeable hand piece.

As depicted in FIGS. 5B and 5C, in one embodiment the board 49 includes an encoded chip 51 and connection pad 53. The chip is typically encoded with an identifying code that is unique to each hand piece as well as code identifying to which of the three types (i.e., about right-angle tip, contra-angle tip, and hollow waveguide) of hand piece the recognition chip is attached. When the interchangeable hand piece 5 is attached to the laser system 3 a spring pin 55 can make a contact with the contact pad 53 on the recognition board 49 providing electrical communication with the chip, allowing a system computer to read the code contained in the encoded chip 51.

Communication of the encoded data can be facilitated using an electrically conductive lead 57 that is in electrical communication with a slip ring to allow for electrical continuity between the rotating and stationary elements of the laser system 3. The slip ring typically includes two rings. A brush ring 59, including spring contacts 60, and a track ring 61, including an electrically conductive track. The electrically conductive track on the track ring 61 may make a contact with the spring contacts 60 of the brush ring 59 throughout a complete rotation of the hand piece 5, allowing for electrical communication of the encoded data regardless of the rotational orientation of the interchangeable hand piece 5.

Figure 5D:
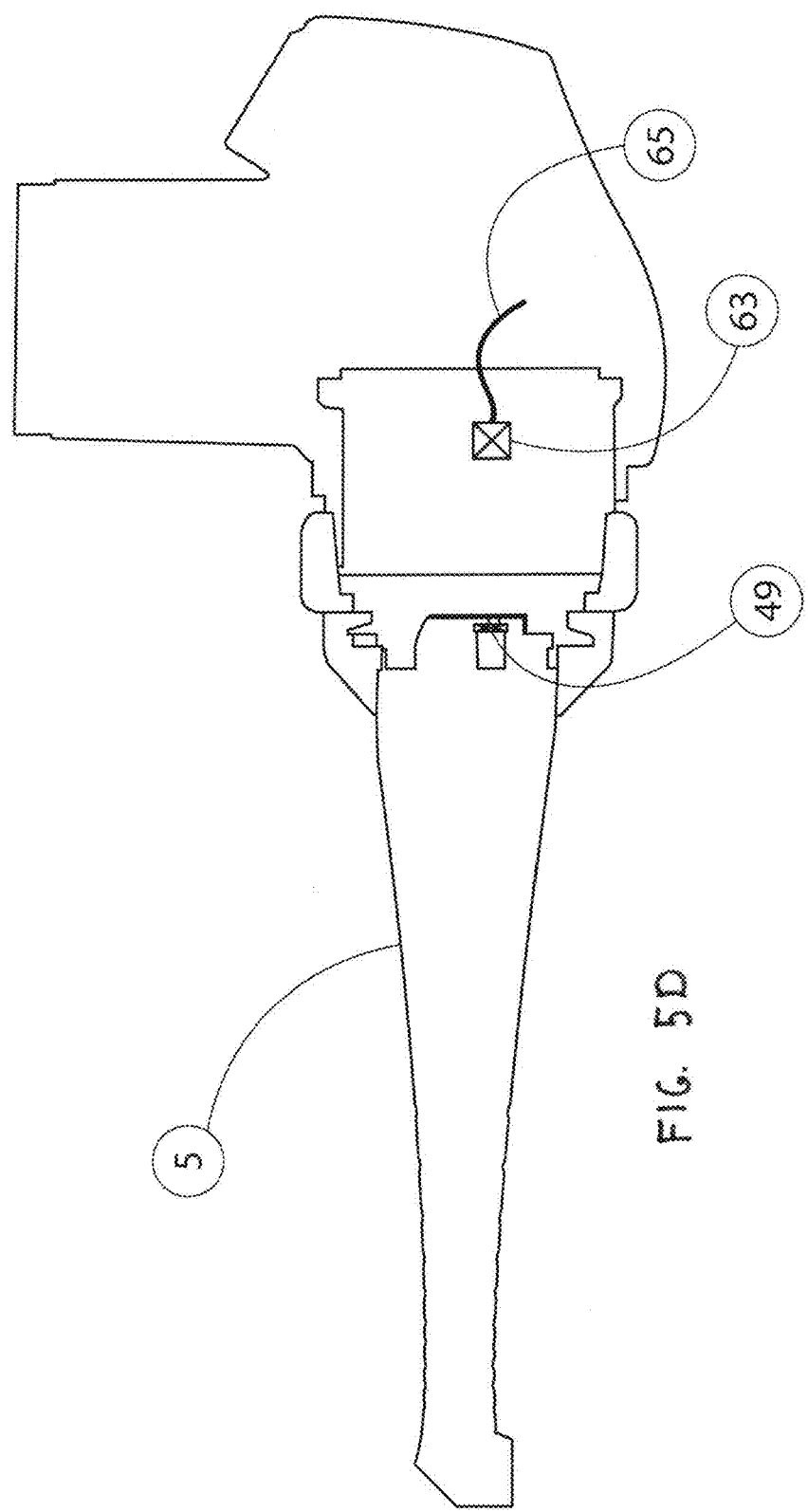

As schematically depicted in FIG. 5D, an active radio frequency (RF) receiver 63 enables communication with the recognition board 49 without a direct electrical connection between the interchangeable hand piece 5 and the laser system 3. In this embodiment, the recognition board 49 includes a passive RFID tag. The active RF receiver 63 is connected to the laser system 3 directly with a communications wire 65.

Figure 6A:
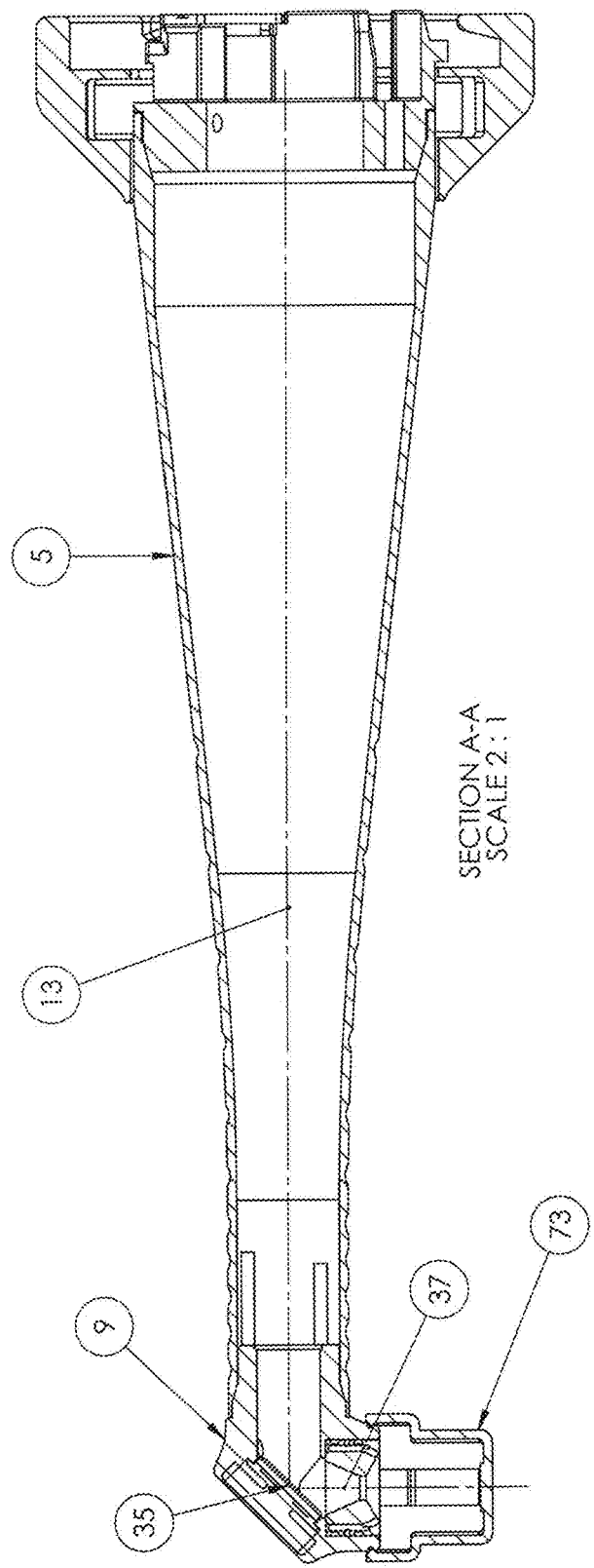

With reference to FIGS. 6A and 6B, the alignment of the laser beam emerging from the tip of a hand piece can be tested using an alignment disc 73. The alignment disc 73 is attached to the end of the about 90° hand piece tip 9. When thus attached, the alignment disc 73 is designed to be substantially concentric about the second optical axis 37. The alignment disc 73 has a target 75 (e.g., a crosshair) marked on the surface that faces the hand piece tip when attached thereto. The alignment disc 73 and the target 75 can be made using a material that is marked when irradiated by a treatment and/or marking laser. This allows the user to ensure alignment of the focused laser beam and beam guidance system. For example, if the laser beam generates a mark 77, which is aligned with the target 75, the system is likely to deliver laser beam to the selected dental treatment area. If the laser beam generates mark 79, however, an adjustment to the beam guidance system may be necessary such that the laser beam will focused at or near the center of the target 75 on the alignment disc 73.

With reference to 6C, in one embodiment, an alignment attachment 63 is affixed to the end 16 of the hand piece. The alignment attachment may include a beam dump 65. The beam dump is positioned under the beam exit 45, and can absorb the laser power, e.g., preventing any stray reflections. A thermal paper burn card 67 may be used to visibly detect the location of an infrared laser beam. Placing the thermal paper burn card 67 between the beam dump 65 and the beam exit 45 allows the beam to be safely directed toward the thermal paper burn card so as to detect the presence of the beam and the target thereof. Energy that burns through the thermal paper burn card is safely absorbed by the beam dump. The alignment attachment allows a user to detect any misalignment of the main and mating optical subsystems prior to clinical use.

For example, the treatment laser beam is expected to be aligned collinearly with a targeting laser beam in the visible spectrum, to allow the operator to target the treatment laser beam to the selected areas. Any misalignment between the targeting laser beam and the treatment laser beam may result in the irradiation of tissue not selected for treatment. This risk can be mitigated by affixing the alignment attachment, noting a location of the targeting beam on the surface of the thermal paper burn card, firing the treatment laser, and ensuring that the resulting burn in the burn card is substantially at the same location at which the treatment laser beam impinged upon the thermal paper burn card.

In some instances, even if the optical axis 26 in the main chamber and the mating optical axis 41 in the hand piece are co-linear, and thus aligned, when the hand piece is affixed to the main chamber, there can be a misalignment between the two optical axes 26, 41 when the hand piece is rotated to a different angular position, e.g., to direct a laser beam to a different treatment area. Alternatively, even if the optical axis 26 in the main chamber and the mating optical axis 41 are co-linear, and thus aligned, when the hand piece is affixed to the main chamber in one angular position, the two axes 26, 41 may not be aligned if the hand piece is affixed to the main chamber in a different angular position.

Specifically, the mating optical axis 41 in the hand piece may be aligned at a small angle (e.g., 0.2 degrees, 0.5 degrees, 1 degree, 3 degrees, 5 degrees, etc.) relative to the optical axis 26 in the main chamber. Such misalignment can occur, e.g., because a cross-section of a hand piece and/or the corresponding O rings may not be perfectly symmetrical about the mating optical axis 41. Similarly, the cross-section of the main chamber and/or the corresponding O rings may not be perfectly symmetrical about the optical axis 26, thereby causing the misalignments described herein. An angular encoder in combination with a controller can be used to correct for or at least reduce such misalignment errors.

In one embodiment, the angular orientation of a hand piece relative to a main chamber is sensed by an angular measurement sensor when the hand piece is affixed to the main chamber. The angular measurement sensor may include an optical sensor that includes a light source and photo detector, positioned in the main chamber and an optically encoded disc positioned on the hand piece. When the hand piece is affixed to the main chamber, the optically encoded disc can be read by the optical sensor. The optically encoded disc may contain an optical pattern that produces a unique code that relates the angular orientation of the disc relative to the optical sensor located in the main chamber and, accordingly, the angular orientation of the hand piece relative to the main chamber.

Alternatively or in addition, the angular measurement sensor may include a magnetic encoder. The magnetic encoder may include a series of magnetic poles located on the hand piece and a magnetic sensor, such as a magneto-resistive or Hall Effect sensor, positioned on the main chamber. Typically, the angular positions of the magnetic poles relative to the magnetic sensor are sensed thereby when the hand piece is affixed to the main chamber, so as to determine the angular orientation of the hand piece relative to the main chamber.

In one embodiment, the angular measurement sensor includes a capacitive encoder. A typical capacitive encoder includes an electrically conductive asymmetrically shaped disc that is positioned on the hand piece. Two electrodes are disposed on the main chamber such that a contact is made between the asymmetrically shaped disc and the two electrodes when the hand piece is affixed to the main chamber. A change in the angular orientation of the hand piece relative to the main chamber generally changes the orientation of the asymmetrically shaped disc relative the two electrodes of the capacitive encoder, resulting in a change the capacitance between the two electrodes. Thus, a measurement of the capacitance between the two electrodes can provide a measure of the angular orientation of the hand piece relative to the main chamber.

In some embodiments, the angular measurement sensor includes an electromechanical encoder. The mechanical encoder includes an insulating disc having a number of openings, and a number of electrical pads behind such openings. Each of the electrical pads is in electrical communication with a corresponding electrical sensor such as a switch. The insulating disc may be located on the main chamber. The electromechanical encoder also includes a row of several sliding male contacts that may be positioned on the hand piece such that the sliding male contacts interface with the insulating disc when the hand piece is affixed to the main chamber. The hand piece when affixed at different angular orientations relative the main chamber allows for different male contacts to establish physical contacts with different electrical pads. The angular orientation of the hand piece relative to the main chamber may then be determined based, at least in part, on the one or more electrical connections made by the male contacts with the pads.

In various embodiments, the angular orientation of the hand piece relative to the main chamber, as sensed by a sensor, is read by a controller. Each angular orientation may be associated with an alignment error representing an angle between the optical axis in the main chamber and the mating optical axis. Typically, about a 180 degree angle between the two axes represents a proper alignment, though it should be understood that a different angle, e.g., 175 degrees, 160 degrees etc., can also represent a proper alignment, depending on the shape of the hand piece and location of the turning optic therein. A deviation from the angle representing a proper alignment indicates the alignment error that corresponds to a sensed angular orientation of the hand piece relative to the beam. The alignment errors corresponding to different angular orientations of the hand piece can be represented as a look up table or as a mathematical function of the angular orientation.

In various embodiments, a controller controls a beam guidance system, based at least in part on the alignment error. The beam guidance system may include galvanometers having mirrors reflecting the laser beam. The mirror positions, that determine the position of the focal point of the laser beam, may be servo-mechanically controlled by the galvanometers and the controller. If the optical axis in the main chamber and the mating optical axis in the hand piece are misaligned, as determined from an angular encoder reading, the initial position of one or more mirrors can be adjusted by the controller and the galvanometers according to the alignment error corresponding to the received sensor reading. As such, the focal point of the laser beam can be shifted back to substantially the same location at which the focal point would occur when the two axes are properly aligned.

Rotationally Orientable, Non-Freely Rotating Hand Pieces

The hand piece described above can direct both a treatment laser beam and a coolant to a treatment area. The hand piece can also direct a targeting or marking laser to the treatment area. The hand piece can freely rotate relative to a main chamber of a laser-beam delivery system while maintaining a fluidic communication between a fluid supply subsystem in the main chamber and a mating fluid supply subsystem in the hand piece. Using the freely rotating hand piece, an operator can conveniently and accurately direct the laser beam to a treatment area without causing significant discomfort to the person being treated.

The free rotatability of the hand piece can, however, result in an accidental, unintended rotation of the hand piece, causing the laser beam to be directed to an area not selected for treatment. A rotation of the hand piece can also potentially cause a slight misalignment of an optical subsystem in the main chamber with a mating optical subsystem in the hand piece, resulting in the laser beam being directed to a slightly different location other than the one selected by the operator. Improved systems and methods are therefore described herein to address one or both of these minor issues.

In various embodiments, a hand piece can be oriented at various angular positions relative to a main chamber while maintaining a fluidic communication between a fluid supply subsystem in the main chamber and a mating fluid supply subsystem in the hand piece. The hand piece can be locked in a selected position, so as to reduce the risk associated with accidental, unintended rotation of the hand piece. The optical subsystems in the hand piece and the main chamber can be aligned based at least in part on the angular position of the hand piece, as determined using a sensor.

With reference to FIGS. 7A-7C, a main chamber 11, having a main optical subsystem 13 and a primary fluid supply system 15, is affixed to a hand piece 16. In one embodiment, the optical subsystem includes an articulating arm 17 through which a laser beam exits toward a first galvanometer mirror 19. The first galvanometer mirror is attached to a shaft of a first galvanometer 21. The angular orientation in a first axis of the first galvanometer mirror and, therefore, the laser's angle of incidence onto the first galvanometer mirror relative to the first axis is servo-mechanically controlled by the first galvanometer. The first galvanometer mirror is generally orientated so that the beam once reflected off the first galvanometer mirror is directed toward a second galvanometer mirror 23, which is attached to a shaft of a second galvanometer 25. The angular orientation in a second axis of the second galvanometer mirror and, therefore, the laser's angle of incidence onto the second galvanometer mirror relative to the second axis is servo-mechanically controlled by the second galvanometer. The second galvanometer mirror is generally oriented so that the beam once reflected off the second galvanometer mirror is directed along an optical axis 26, toward and through a first focusing optic 27 that is generally centered along the optical axis 26. The first focusing optic 27 generally has a concave curvature. The first focusing optic 27 defocuses the beam, increasing the beam width as the beam is directed toward and through a second focusing optic 29, that is also generally centered around the optical axis 26. The second focusing optic 29 has a generally convex curvature and may be larger in diameter than the first focusing optic 27 to allow for the increased beam width. The curvatures and locations of the first and second focusing optics are selected such that the beam is focused outside the hand piece at a selectable distance from an orifice thereof.

In one embodiment, a primary fluid supply system 15 includes a number of tubes providing fluidic communication to fluid sources such as air and coolant pumps. These tubes may be connected to several fittings 31, and may provide fluidic communication to a primary fluid manifold 33. The primary fluid manifold can provide a singular fluidic communication to a corresponding number of radial ports 35.

The hand piece, 16, having a mating optical subsystem 37, and a secondary fluid supply system, 39, is shown affixed to the main chamber 11. The mating optical subsystem has a mating optical axis 41, and includes a turning mirror 43 and a beam exit 45. For delivery of the laser beam to a desired target location, it is necessary that the mating optical subsystem be aligned substantially with the optical subsystem of the main chamber when the hand piece is affixed to the main chamber. One or more locating O rings 47 and perpendicular shoulders 49, 51 can provide an initial alignment. The locating O rings are compressed between a bore and a shaft of the main chamber and hand piece which are alternatively concentric with the optical axis 26 and the mating optical axis 41. This can provide a concentric alignment between the optical subsystem and the mating optical subsystem at the axial position of the locating O rings, i.e., when the hand piece is affixed to the main chamber the optical axis 26 and the mating optical axis 41 are substantially co-linear.

To this end, while affixing the hand piece to the main chamber it is seated on a shoulder 49. The shoulder 49 is perpendicular to the optical axis 26 of the optical subsystem in the main chamber. A second shoulder 51 is located on the hand piece and is perpendicular to the mating optical axis 41. When affixed, the second shoulder 51 may be seated flatly on the first shoulder 49, thus aligning the mating optical axis 41 parallel to or co-linear with the optical axis 26 of the optical subsystem of the main chamber.

In one embodiment, the beam travels as centered around the mating optical axis 41 of the affixed hand piece and reflects off a turning mirror 43. The turning mirror is generally centered on the mating optical axis of the hand piece and has an angular orientation such that the beam is reflected through the beam exit 45 toward a treatment area. In another embodiment, a turning mirror is not used; instead the beam exit is generally centered around the mating optical axis 41.

In various embodiments, a second, mating fluid supply system is provided in the hand piece. The mating fluid supply subsystem may include a number of annular grooves 49 that are in fluidic communication via several radial ports 51 with corresponding axial ports 55, and various internal tubes 57. The internal tubes are routed along the length of the hand piece toward a tip thereof. The grooves are sealed on both sides by sealing O rings 53.

When the hand piece is affixed to the main chamber, the annular grooves, which are in fluidic communication with the second, mating fluid supply system, maintain a fluidic communication with the radial ports of the fluid supply system of the main chamber regardless of the angular orientation of the hand piece relative to the main chamber.

Figure 8A:
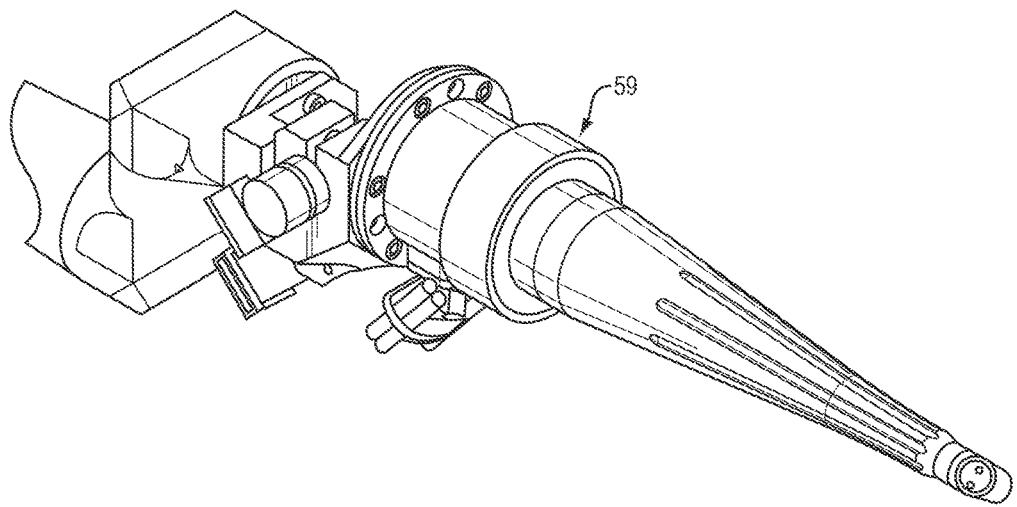
FIGS. 8A and 8B depict various exemplary orientations of the hand piece and the main chamber depicted in FIGS. 7A and 7B.
Figure 8B:
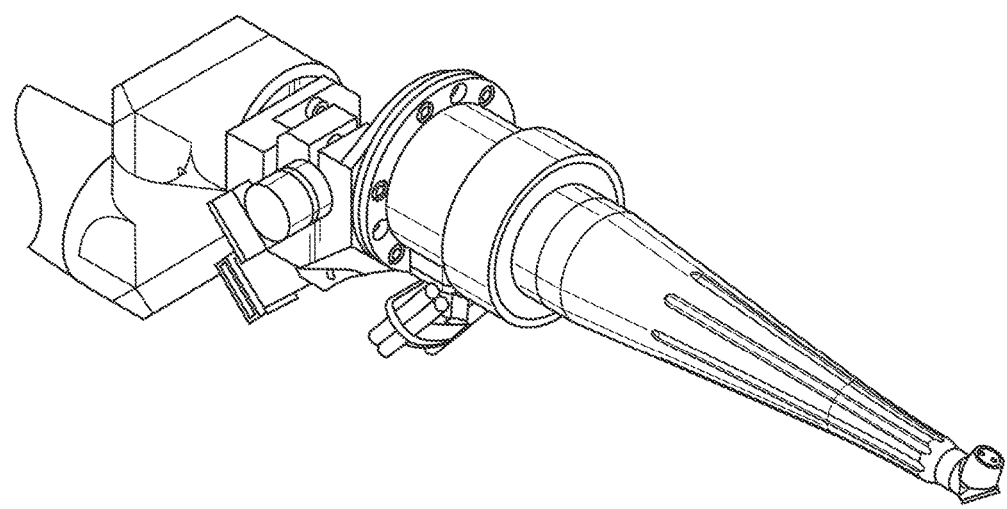

In one embodiment, the hand piece may be attached to the main chamber at any selectable angular orientation while maintaining a fluidic communication between the fluid supply system in the main chamber and the second, mating fluid supply system. An alignment between the optical subsystem and the mating optical subsystem may be maintained as well. FIGS. 8A and 8B show the hand piece affixed to the main chamber at two different angular orientations. In one embodiment, once affixed to the main chamber the hand piece may be rotated to a selected angular orientation, and locked in that location using a threaded locking nut 59.

Figure 8C:
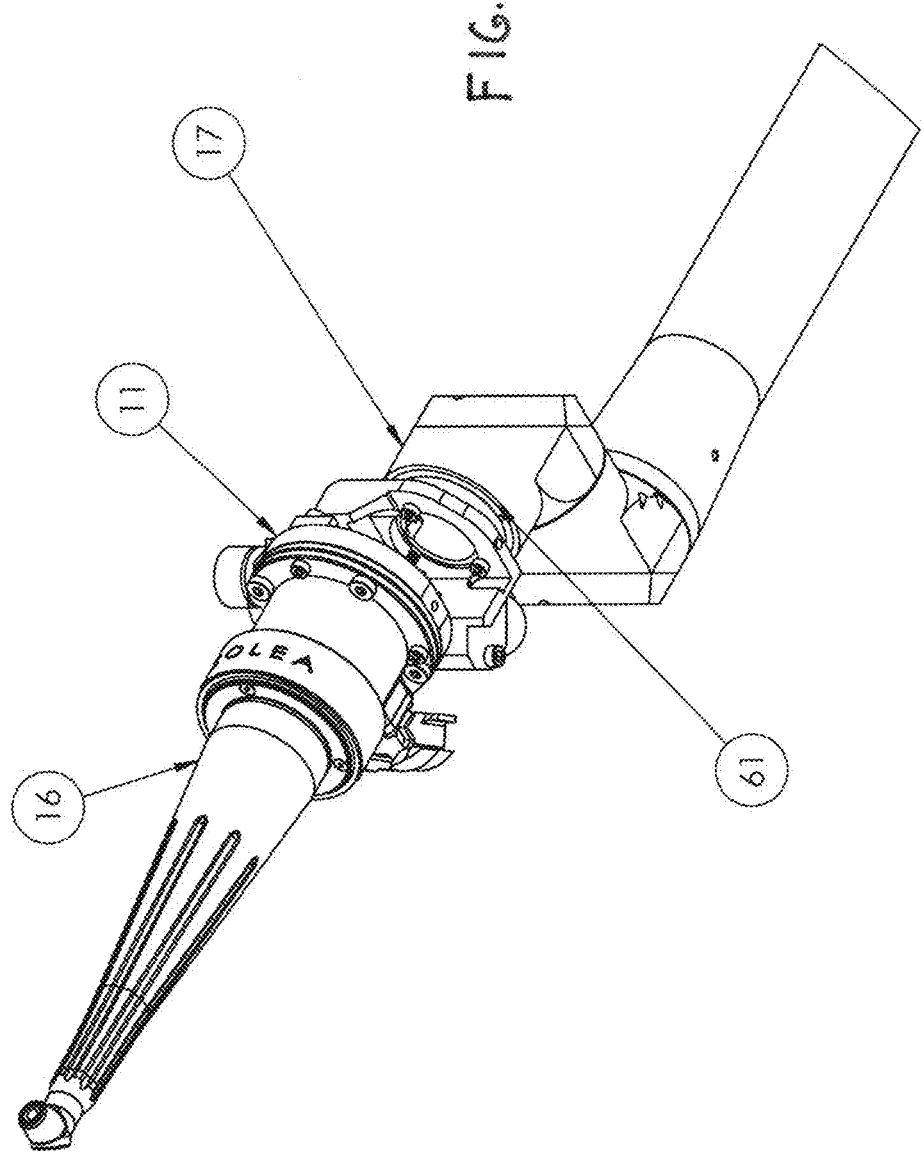
FIG. 8C depicts the hand piece and the main chamber depicted in FIGS. 7A and 7B, coupled to an articulating arm, according to one embodiment.

With reference to FIG. 8C, the main chamber 11 may be attached to the articulating arm 17 via a rotational joint 61. The rotational joint may allow for small changes in angular orientation (up to about 1 degree, 2 degrees, 5 degrees, etc.) of the hand piece relative to in initial position thereof when the hand piece and main chamber are locked together. The rotational joint can also allow for larger changes in the angular orientation, e.g., 30°, 40°, 90°, etc. This can provide to the operator a degree of freedom of movement of the hand piece, so that it can be conveniently oriented to direct a laser beam to a selected location, while substantially preventing any undesired or unintended free movement because the hand piece and the main chamber are locked together.

Pulsing and Control of Parameters

A variable foot pedal may be attached via USB to the internal computer of the dental laser apparatus and software may be used to transform sensed changes in the peripheral foot pedal depression to corresponding changes in process variables. The foot pedal can also be used as an input to the software of the computer of the dental laser apparatus. Default parameters such as fluid flow rate, laser power, scan speed, graphical zoom, and other variables available to an operator may be changed using the foot pedal during treatment. Various parameters of the dental laser apparatus can be controlled using a variable switch such as a foot pedal that provides for varied control of laser power by varying parameters such as pulse frequency, pulse width, laser scan rate, jump speed, and the number of pulses per spot. The switch (e.g., foot pedal) may also control the fluid flow by varying pump speed and/or fluid pressure to control the delivery of the mist. In general, the more the depression of the foot pedal the greater the laser power delivered, the speed of beam scanning, and/or the volume of the mist flow. The use of the variable foot pedal as an analogue periphery to the operating system and/or software of the dental laser system can provide for fast and convenient interactions with the system without need to stop the procedure to change one or more parameters of the laser treatment.

The variable foot pedal 7 (an input device, in general) can also set and control system parameters in an off-line mode, i.e., when a treatment using the laser system is not in progress. Off-line modification of one or more parameters is typically performed prior to treatment. System variables that can be set in the off-line include coolant flow rate, air pressure, beam pattern size, and laser power settings. Using the foot pedal to set system parameters prior to treatment allows for hands free initialization of the dental laser system. One or more parameters set in the off-line mode can be adjusted using the foot pedal during treatment. For example, the flow of fluids to the interchangeable hand piece 5 is controlled continuously or discretely using the foot pedal.

In treating a tooth using various embodiments of the laser dental system, the operator (e.g., a dentist) typically directs the tip of the hand piece to a region of the tooth and activates the laser. Laser pulses are then delivered to the selected region according to a pattern such as a spiral pattern, zig-zag scanning pattern, random pattern, etc. Specifically, the laser beam impinges upon several spots within the selected region according to the user selected pattern. The movement of the laser beam can be controlled by a galvo/servo-mirror assembly, which is configured to scan the selected region such that laser pulses are not delivered continuously (e.g., for a duration of a few milliseconds) to a single spot. This avoids or reduces overheating and potentially harmful ablation of a spot on the tooth or gum. The scanning using the galvo/servo-mirror assembly can also ensure that adequate energy is delivered in a substantially uniform manner to the entire selected region such that the ablation within the region is even. Thus, the galvo/servo-mirror assembly allows a user to evenly and safely treat a selected region, without having to frequently move the hand piece, which may be necessary to avoid overheating without the galvo/servo-mirror assembly. The user may simply hold the hand piece in one position for a selected duration (e.g., a few seconds, one or a few minutes, etc.)

The operation of the galvo/servo-mirror assembly is typically closely related to the characteristics of the pulse sequence. These characteristics may include pulse rate, pulse width, energy per pulse, etc. For example, if the user increases the pulse rate by pressing on the foot pedal, it may be desirable to increase the rate of mirror movement in the galvo/servo-mirror assembly, to prevent too many pulses in a single spot and resultant overheating. Similarly, if the user lowers the pulse rate, it may be desirable to decrease the rate of mirror movement, so that the entire selected region is treated effectively. In various embodiments, the galvo-mirror assembly control parameters are selected according to the characteristics of the sequence of pulses, selected by the movement of the foot pedal.

Methods and systems to automatically adjust a galvo/servo-mirror assembly according to selected treatment parameters (such as pulse rate, area of the selected region, shape of the pulse, pulse energy distribution, etc.) were described in co-pending U.S. patent application Ser. No. 13/603,165, titled "Laser Based Computer Controlled Dental Preparation System," filed on Sep. 4, 2012, which is incorporated herein by reference, and the disclosure of which forms a part of this patent application.

One embodiment of the present invention uses a pulsed laser source e.g., a pulsed 9.3 um CO2 laser. The beam, focused to a small spot size on the order of, e.g., 100 μm, 250 μm, etc., may be scanned using galvo/servo controlled mirrors, and directed to the treatment area. The pulse width and the frequency of the pulses generally controls the average laser power delivered to the treatment area. The speed of the beam scanning can be determined by the speed of jump from point to point. As such, the number of pulses at each location point can be controlled to control the amount of laser energy to be delivered to that location. The flow of the fluids to the hand piece tip may be controlled using electronic pumps and regulators. The values of these variables may be controlled, e.g., using software executing on the system computer.

Figure 9A:
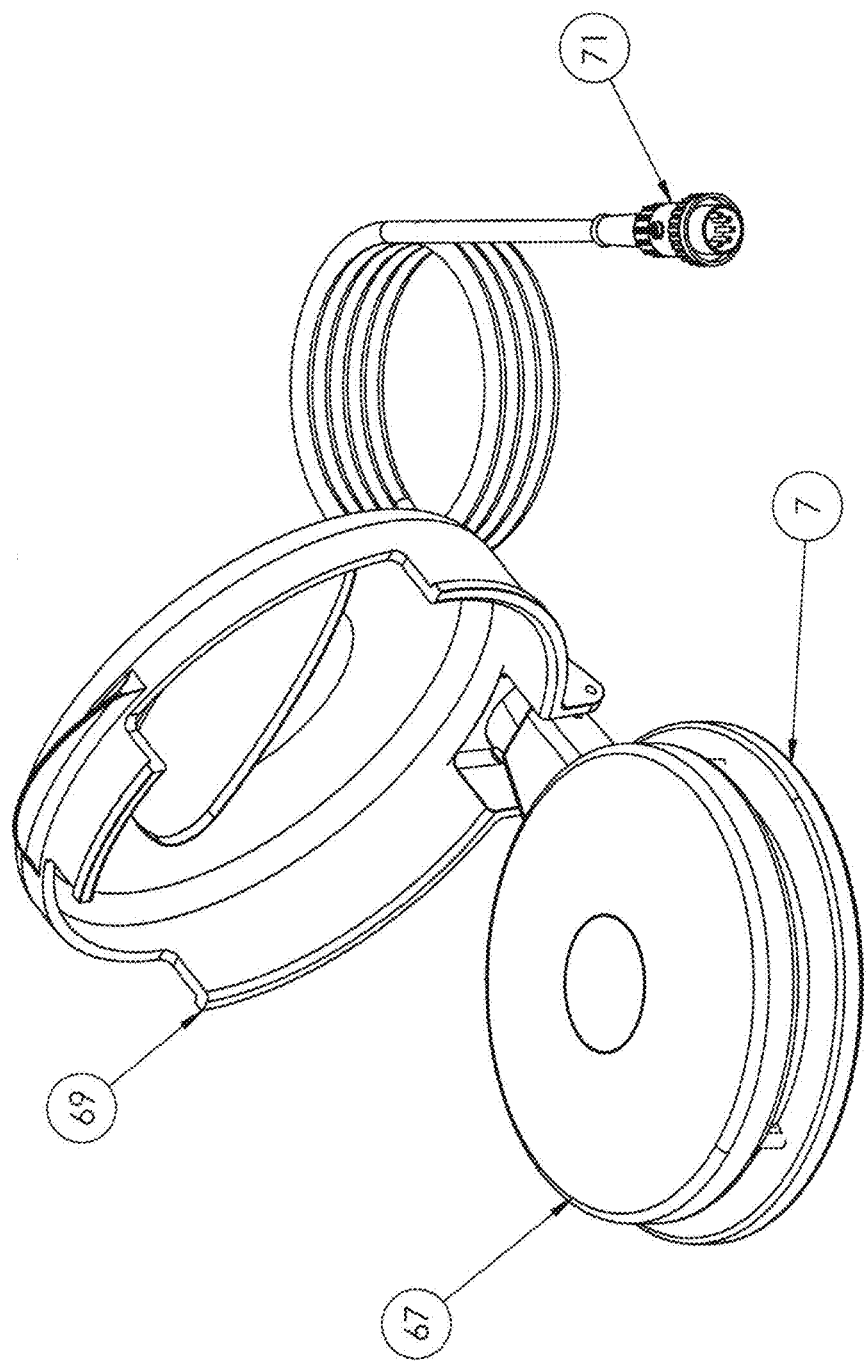
FIG. 9A depicts components of a foot pedal, according to one embodiment.

The repetition rate of the laser pulses may be controlled in real time using a variable foot pedal 7. FIG. 9A shows the variable speed foot pedal 7 with a round foot switch 67 that is accessible from substantially all directions, a protective cover 69, and a foot pedal plug 71 that connects to the dental laser system 7.

FIG. 9B illustrates three different cases demonstrating the function of the variable foot pedal 7 on a dental laser system 3 according to one embodiment. In Case A, the variable foot pedal 7 is maintained in an un-depressed state. In this state no pulse signal is sent to the laser source and the laser does not pulse. In Case B, the foot pedal 7 is lightly depressed and, correspondingly, laser pulses at a moderate repetition rate are delivered via the hand piece. In Case C, the foot pedal 7 is fully depressed and, correspondingly, laser pulse at a relatively high repetition rate are delivered via the hand piece.

Figure 10A:
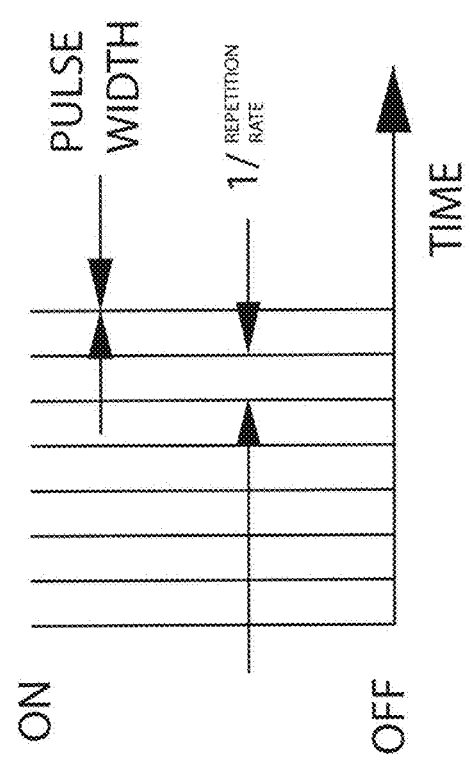
FIGS. 10A and 10B schematically illustrate two pulse patterns according to two embodiments.

With reference to FIG. 10A, the laser pulses may have a substantially uniform single frequency. In general, there are two variables that can describe the pulse pattern for a single frequency, namely, the pulse width and the pulse repetition rate. The pulse repetition rate of the laser pulses can be varied and controlled by the foot pedal 7. In some embodiments, the pulse width is variable and controlled by the foot pedal 7.

Figure 10B:
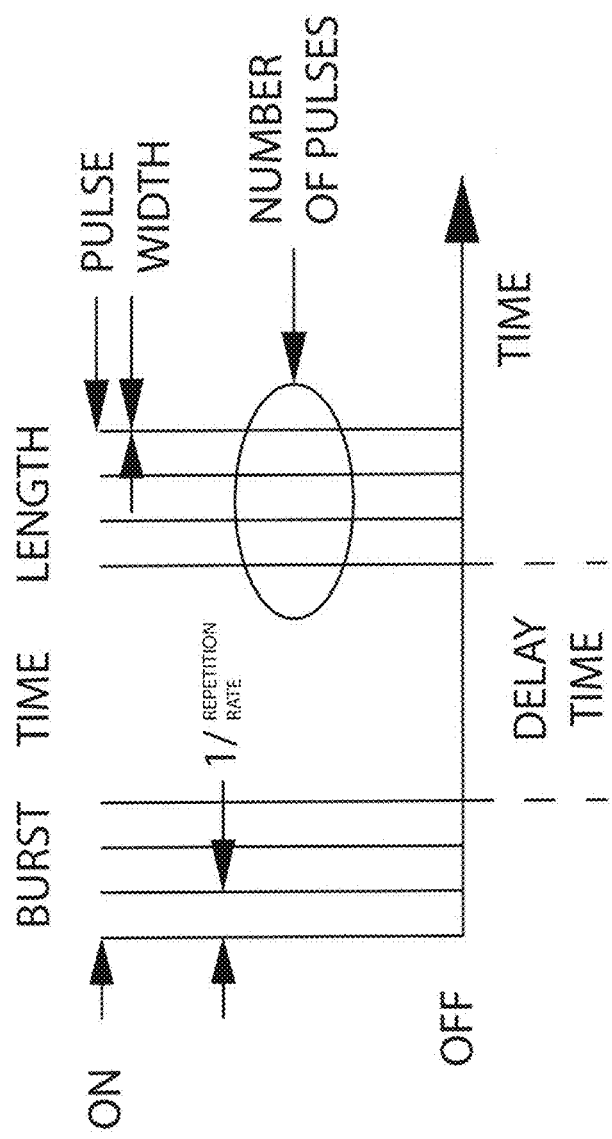

The laser source may also be triggered in a burst pulse pattern that includes a sequence of bursts of laser pulses. Each burst includes an array of laser pulses, and the burst is followed by a delay period, as schematically depicted in FIG. 10B. The burst pulse pattern generally allows for the treated surface to cool through convection in between bursts of pulse arrays of irradiative energy, preventing or at least decreasing any thermal damage to the tissue being treated and/or any surrounding tissue. The burst pattern is typically described by a number of parameters, each of which may be variable and controlled using the variable foot pedal 7. The parameters determining the burst pulse pattern may include: burst duration (ON interval), i.e., the duration of the sequence of pulses in a single burst; number of pulses per burst; pulse frequency, i.e., the rate at which pulses are delivered during a sequence of pulses within a single burst; delay time (OFF interval), i.e., the length of time between two consecutive sequence of pulses; and pulse width, the duration of each individual laser pulse.

The pulse frequency can be increased by decreasing the pulse width, the delay between successive pulses, or both. The pulse width can be increased and the delay between pulses can be reduced by an amount greater than the increase in the pulse width such that the pulse frequency would increase. In some embodiments, when the pulse frequency is varied independently of all other parameters, the pulse width and delay time between two consecutive bursts are not changed significantly. Similarly, if the pulse width is changed but the pulse frequency and the number of pulses per burst remain unchanged, the burst duration remains unchanged. Each of the parameter described herein can be varied together with one or more other parameters, or independently, i.e., without changing any other parameter.

Removal rate is a function of irradiated energy directed to the treatment area (e.g., a tooth), which is typically determined by energy per burst times the number of bursts per unit of time. The amount of energy per burst per unit of time can be determined by the independent parameters: number of pulses per burst, pulse frequency, and pulse width. The number of bursts in a unit of time is determined by: (a) the independent parameter, delay time, and (b) the burst duration, which can be a function of number of pulses per burst, pulse frequency, or pulse width, or a combination of any two or all three of these parameters.

In one embodiment, the pulse frequency is variable and controlled with the level of depression of the foot pedal while keeping the number of pulses per burst substantially constant. Increasing the pulse frequency but delivering the same number of pulses in a single burst can result in decreasing the burst duration. A reduction of the burst duration while maintaining the number of pulses per burst and the pulse width substantially constant can, effectively, increases the rate of laser energy directed to the treatment area, resulting in an increased removal rate.

In another embodiment, the number of pulses per burst is variable and controlled by the foot pedal control while the burst duration is maintained substantially constant. Increasing the number of pulses per burst can thus increase the amount of laser ON time during a single burst array, and can correspondingly increases the rate of laser energy directed toward the treatment area. The delay time can also be varied and controlled with the foot pedal. Decreasing the delay time between burst arrays typically increases the duty cycle of the laser, the irradiative power directed toward the treatment area, and the material removal rate, while reducing the time for convective heat removal from the treatment area and surrounding tissue between burst arrays.

In another embodiment, the pulse width is variable and controlled with the variable foot pedal. If the number of pulses per burst is not decreased, increasing the pulse width increases the amount of irradiated energy being directed to the treatment area. A change of the pulse width also increases the amount of energy delivered to the treatment area in a single pulse.

In one embodiment a beam guidance system, mirrors attached to galvanometers/servos are employed to scan the laser beam on a treatment surface. The beam guidance system may be used to scan a predetermined pattern, such as a spiral, on the treatment surface optionally enlarging the area that is affected by the laser. The beam guidance system can move the focused spot of the laser beam discretely from a first location to second location, in a specified amount of time—a parameter called jump interval. The beam guidance system stops at a certain position as the laser fires, before moving to the next position according to the pattern to be traced by the laser beam. The amount of time for which the beam guidance system stays in each position is a parameter called dwell time.

Figure 10C:
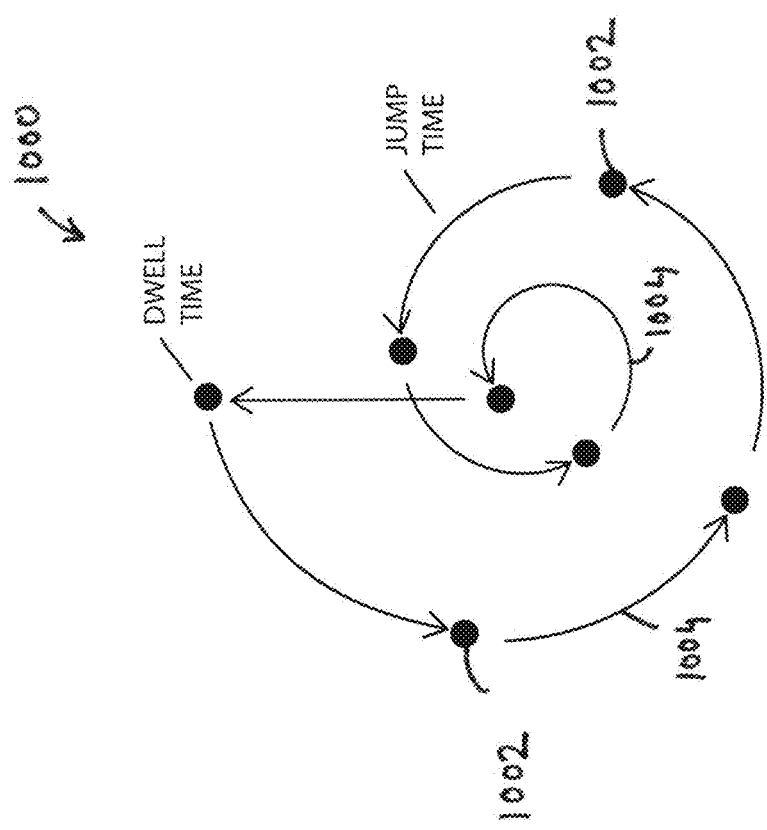

In FIG. 10C depicting an exemplary scanned beam pattern 1000, the locations of the treatment area towards which the beam guidance system directs the laser beam during each dwell time are shown by dots 1002. The paths taken by the beam guidance system from one location to the next location are indicated by arrows 1004. The movement between two locations generally occurs during a jump interval. One parameter of the rate of scanning of the beam guidance system when moving discretely from one position to another is the longitudinal or angular distance traversed from one irradiated location to the next by the beam per one jump interval.

The beam guidance system may be employed with a burst pulse laser pattern or with a single frequency pulse laser pattern. When employed with a burst pulse laser pattern, the beam guidance system directs the beam to a location and dwells in the corresponding position as one or more burst arrays are delivered to that location. Subsequently, the beam guidance system directs the beam to the next location during the delay time, i.e., the delay between the sequence of pulses of two bursts. In some embodiments, a single burst is delivered per location and, as such, the dwell time of the beam guidance system is related to the burst duration and the jump interval of the beam guidance system is related to the delay time of the burst pulse pattern. In these embodiments a change of the pulse frequency (e.g., using the foot pedal) can vary the burst duration and, accordingly, the dwell time of the beam guidance system. This is because the burst duration is the number of pulses per burst (which may remain unchanged) times the pulse period, which is inversely related to the pulse frequency. Therefore increasing the pulse frequency can decrease the burst duration and, hence, the dwell time of the beam guidance system. The decrease in dwell time can result in an increase of the number of locations toward which the beam guidance system directs the laser in a certain amount of time while not affecting the speed of the beam guidance system movement between locations, as the jump interval may remain unchanged.

In some embodiments the delay time of the burst pulse pattern can be varied and controlled using the variable foot pedal. A change in the delay time typically varies the jump interval of the beam guidance system, as well. In these embodiments, decreasing the delay time between burst arrays increases the number of locations the beam guidance system directs the laser toward in a certain amount of time and decreases the jump interval for the beam guidance system, resulting in increasing the speed of the beam guidance system.

In another embodiment, the number of pulses per burst is variable and can be controlled by the foot pedal. In this embodiment, the dwell time of the beam guidance system is related to burst duration, which is the number of pulses per burst times the pulse period, which is the reciprocal of the pulse frequency. Therefore, an increase in the number of pulses per burst can increases the dwell time of the beam guidance system while the jump interval and speed of the beam guidance system may remain substantially unchanged.

In yet another embodiment, the pulse width of the burst pulses is variable and controlled by the foot pedal. In this embodiment a change in the laser pulse width can alter the dwell time of the beam guidance system, because the change in the pulse width can cause a change in the burst duration. The jump interval and speed of the beam guidance system may remain unchanged.

Figure 10D:
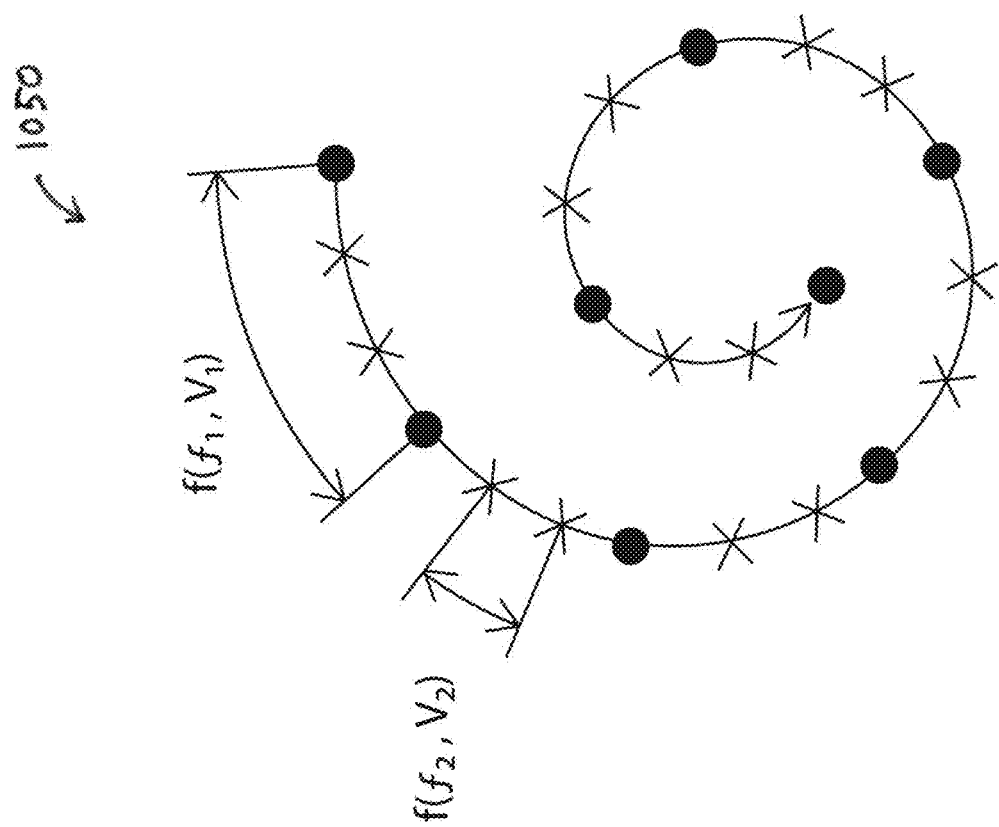

With reference to FIG. 10D, in some embodiments, the beam guidance system may not move the beam discretely from one location to another, dwelling at each individual location. Instead, the beam guidance system moves continuously in a pattern, such as a spiral pattern 1050. The laser pulses may be delivered in a uniform, substantially single frequency pattern. When employed with a single frequency pulse laser pattern, the jump interval of the beam guidance system is generally related to the laser pulse repetition rate and the dwell time is typically related to the laser pulse width. In one embodiment, increasing the pulse repetition rate through increased foot pedal depression can decrease the jump interval and can increase scanning rate, i.e., the speed of the beam guidance system, and the number of locations to which the beam is directed in a given amount of time. Increasing the pulse width of the single frequency laser pulse pattern may increases the dwell time the beam is directed at a particular location. The scanning rate of the beam guidance system may remain unchanged when the dwell time is changed.

The distance between successively irradiated locations and, therefore, the number of irradiated locations can be determined by the repetition rate of the single frequency pulse pattern relative to the speed of continuous movement of the beam by the beam guidance system. An increase in the repetition rate of the single frequency pulse pattern (i.e., the frequency of pulses), using the foot pedal, for example, while maintaining the speed of the beam guidance system can decrease the distance between successively irradiated locations of the treatment area, increasing the number of irradiated locations within the beam guided pattern and the amount of irradiative power directed to the treatment area.

In another embodiment the speed of the beam guidance system is variable and controlled with the foot pedal while a substantially constant pulse repetition rate is maintained. This can affect the distance between irradiated locations and number of irradiated locations within the beam guided pattern, but the irradiative power directed toward the overall treatment area may remain substantially unchanged, even though, the speed of the beam guidance system changes.

In another embodiment the continuous speed of the beam guidance system and the repetition rate of the single frequency laser pulse pattern are both variable and controlled in a substantially fixed proportion to each other using the foot pedal. Varying both the continuous speed of the beam guidance system and the repetition rate of the single frequency pulse pattern in equal proportions allows for the distance between irradiated locations as well as the number of irradiated locations within a beam guided pattern to remain substantially constant as the irradiative power directed to the treatment area is varied.

In another embodiment the pulse width of a single frequency laser pulse pattern is variable and controlled using the foot pedal while the continuous speed of the beam guidance system is maintained substantially constant. Varying the pulse width may vary the irradiative power directed toward the treatment area as well as the size of the irradiated locations. Longer pulse widths can result in larger irradiative locations as the beam guidance system continues to move during the pulse of the laser. For pulse widths that are short relative to the speed of the beam guidance system the change in the size of individual irradiated locations can be negligible and the primary effect of the change in the pulse width may be a change in irradiative power delivered to the treatment area.

With reference to FIG. 10E, if a burst pattern is employed with a beam guidance system that moves the laser beam in a continuous motion, the size of the irradiated locations in the pattern can be determined by the speed of the beam guidance system as well as the burst duration of the burst pulse pattern. The distance between irradiated locations is generally a function of the speed of the beam guidance system and the delay time, i.e., the delay between successive burst arrays in the burst pattern.

In one embodiment, the pulse frequency is varied and controlled, for example, using a joy stick, foot pedal, etc. As the burst duration is generally equal to the number of pulses per burst times the pulse period, i.e., the reciprocal of the pulse frequency, a change in the pulse width independent of pulse frequency, may not result in a change in the burst duration. This can substantially preserve the irradiated locations of the treatment area. The amount of energy delivered to each location may change, however, according to the pulse width. An increase in the pulse frequency can decrease the size of the irradiated spot, because the burst duration may decease and the beam generally moves continuously at a substantially uniform speed along a path.

In another embodiment the speed of continuous movement of the beam by the beam guidance system and the pulse frequency are both varied and controlled in proportion to each other by the variable foot pedal. As such, the size of the irradiated locations of the treatment area may be maintained substantially constant by varying the speed of the beam guidance system as well as the pulse frequency of the laser proportionally. Specifically, as the pulse frequency increases, the burst duration generally decreases, but the size of the irradiated spot can be preserved by increasing the speed of beam movement. The amount of energy directed to the treatment area and time between bursts for cooling can also varied by varying the pulse frequency, if the burst period, i.e., the sum of the burst duration and time delay, is maintained substantially unchanged by adjusting the time delay, i.e., the delay between the sequence of pulses in successive bursts.

In some embodiments the number of pulses per burst is variable and controlled by the foot pedal and the beam guidance system is configured to move the beam continuously at a generally uniform speed. The pulse frequency may be substantially constant. In this embodiment, the size of the irradiated locations on the treatment area and the energy delivered to each spot and/or the overall treatment area may vary. An increase in the number of pulses per burst can increase the size of the irradiated locations by increasing the burst time and may increase the laser power directed to each location and/or the overall treatment area.

In other embodiments, the speed of the beam and the number of pulses per burst can be varied using the foot pedal. For example, these two parameters can be controlled to be proportional and/or inversely proportional. In these embodiments, the size of the irradiated locations on the treatment area may be maintained generally constant as the number of pulses per burst and lased power directed to the treatment area change. In one embodiment, as the number of pulses per burst decreases, the burst duration may decrease, but the size of the irradiated spot can be maintained by proportionally increasing the speed of movement of the laser beam.

In one embodiment, the burst delay time is varied and controlled by the foot pedal, while the beam is moved continuously and at a substantially uniform speed by the beam guidance system. In this embodiment, the distance between successively irradiated locations of the treatment area may vary with the burst delay time. A longer burst delay time can result in a larger distance between irradiated locations. Alternatively, the speed of the beam and the burst delay time can be varied by the foot pedal, and controlled to be proportional and/or inversely proportional. Therefore, as the delay time increases, the speed of beam movement can be decreased so that the distance between consecutively irradiated spots remains nearly unchanged.

In yet another embodiment, the pulse width of the laser pulses is varied and controlled by the foot pedal while the laser beam is moved continuously at a uniform speed by the beam guidance system. The size of the irradiated locations of the treatment area may remain generally unchanged with the pulse width. As described above, the size of the irradiated locations is a function of speed of beam motion and burst duration, which is equal to the number of pules per burst times the pulse period. Thus, even though the pulse width is changed, if the pulse frequency and number of pulses per burst remain substantially constant, the burst time remains generally constant, maintaining the size of the irradiated locations of the treatment area.

In another embodiment, the speed of the beam motion and pulse width are varied by the foot pedal in a proportional and/or inversely proportional manner. As such, the size of the irradiated locations can be maintained generally constant as the pulse width is varied according to foot pedal control. For example, if the pulse width is decreased, allowing the pulse frequency to increase, the burst duration may decrease, By proportionally increasing the speed of beam movement, the size of the irradiated spot can be maintained substantially unchanged. The amount of laser energy delivered to an irradiation location may decrease, however.

In some embodiments, only the speed of movement of the beam by the beam guidance system is varied and controlled by the foot pedal while the laser burst pattern parameters are not changed substantially. Thus, the size of the irradiated locations, as well as the distance between successive irradiated locations, can vary with the speed of the beam motion. An increase in speed of beam movement can increase the size of the irradiated locations, as well as the distance between successively irradiated locations.

Exemplary Operation

Depending on the dental diagnosis, the operator may choose a dental procedure. The interchangeable hand pieces generally allow an operator to perform any one of a wide array of hard and soft tissue procedures. Via the user interface 4 (depicted in FIG. 1A) and a variable switch (e.g., the foot pedal 7) the operator may set various system parameters for the chosen procedure. The operator may also select a hand piece that is suitable for the chosen procedure. For example, the diagnosis may be a Class 1 to 5 preparation on the occlusal surface of a premolar, and the operator may select a hand piece 5 suitable for this procedure. The operator may then attach the selected hand piece 5 to the main chamber 30 by holding the grip 38 stationary while rotating the bayonet feature 36. Locking the hand piece in place can ensure that spring pin 55 touches the recognition board 49 and allows the system computer to recognize which hand piece 5 is attached, as described above with reference to FIGS. 5A-5D. Once the hand piece 5 is recognized, the user interface 4 may display the system options appropriate for that hand piece 5.

The operator may then chose to use the default system parameter preselected on the user interface 4, or may change any of the parameters within the available settings. For example, the operator may change the pulse width, maximum pulse frequency, and/or laser scan size, shape, etc. The operator may test the alignment of the laser beam, as described with reference to FIGS. 6A-6C. The operator may then place the hand piece tip 9 in the patient's mouth, and may align the hand piece second optical axis 37 with the area to be treated.

Once the hand piece tip 9 is appropriately placed and the user interface 4 parameters are selected, the operator may lift the foot pedal protective cover 69, and may depress the round footswitch 67 partially or completely. Releasing the foot pedal 7 can stop the delivery of laser energy to the treatment area. The operator may then inspect the tooth being treated and choose to treat the tooth further, or may choose to change the system parameters using the user interface 4 before continuing with the treatment. For example, the operator may increase or decrease the air and/or water flow via the user interface 4 so as to change the water mist combination.

Optionally the operator may fully or partially rotate the hand piece 5, typically by spinning the hand piece 5 which rotates the coupling 11 via the locking bayonet 36, in order to align the second optical axis 37 to any feature on the treatment area. For example, to cut interproximally (from the side of a tooth) or to cut an occlusal surface on an upper tooth, the hand piece 5 may be rotated about the optical axis 13. The alignment and treatment steps may be repeated as described above.

The operator may also chose a hollow waveguide or fiber tipped hand piece that may not require air or water for cooling during treatment of the soft tissue. As describe above, once the new hand piece is attached to the main chamber, the system computer may recognize that hand piece and the user interface 4 may display system options available for the new hand piece with the tip 43 (depicted in FIG. 4). The operator may then continue treatment, for example, by aligning the end of the hand piece 43 visually with the area to be treated, or may then place the hollow waveguide or fiber on the soft tissue to be treated. After the treatment is completed the operator may return the foot pedal protective cover 69 to the closed position.

Systems and methods described herein can be used to treat oral tissue, gums and teeth, e.g., to human or animal oral tissue, gums and teeth. Specifically, these systems and/or methods may be used in procedures for removing decay, cutting, drilling or shaping hard tissue, removing and cutting soft tissue, modifying hard tissue for caries inhibition and modifying hard tissue surface conditions to aid in adhesion to hard tissue.

While the invention has been particularly shown and described with reference to specific embodiments, it will be understood by those skilled in the art that various changes in form and detail may be made therein without departing from the spirit and scope of the invention as defined by the appended claims. The scope of the invention is thus indicated by the appended claims and all changes that come within the meaning and range of equivalency of the claims are therefore intended to be embraced.

What is claimed is:

1. A laser-based dental treatment system comprising:
a laser producing a pulsed laser beam;
a galvo-mirror assembly for directing a sequence of pulses of the pulsed laser beam to a first irradiation location of a selected treatment area;
a controller; and
a variable input device connected to the controller for controlling the laser-based dental treatment system, the variable input device adapted to input an adjustment to at least one characteristic of the sequence of pulses based on an operator interaction with the variable input device while the sequence of pulses is being directed to the selected treatment area,
wherein, while the sequence of pulses is being directed to the selected treatment area, the controller adjusts a rate of movement of the galvo-mirror assembly automatically and as a function of the at least one adjusted characteristic of the sequence of pulses such that a size of a next irradiation location after adjustment is made relative to a size of the first irradiation location is unchanged.

2. The system of claim 1, wherein the at least one characteristic of the sequence of pulses is selected from the group consisting of a laser pulse repetition rate, a laser pulse width, and laser energy per pulse.

3. The system of claim 1, wherein adjusting the rate of movement of the galvo-mirror assembly comprises adjusting at least one of a time interval during which the laser beam is moved from a first location to a second location and an amount of time for which the laser beam is maintained in one position.

4. The system of claim 1, wherein the variable input device comprises a foot pedal comprising an upper surface adapted for contact by a foot of the operator.

5. The system of claim 4, wherein the foot pedal is further adapted to adjust power of the pulsed laser beam that is used for dental treatment.

6. The system of claim 1, wherein:
the characteristic comprises a burst duration; and
the controller adjusts the rate of movement by increasing a dwell time of the galvo-mirror assembly if the burst duration is increased and, otherwise, decreasing the dwell time.

7. The system of claim 1, wherein:
the characteristic comprises a duration of time between consecutive bursts of pulses; and
the controller adjusts the rate of movement by increasing a jump interval of the galvo-mirror assembly if the duration of time between consecutive bursts of pulses is increased and, otherwise, decreasing the jump interval.

8. The system of claim 1, wherein:
the characteristic comprises a number of pulses per burst of pulses; and
the controller adjusts the rate of movement by increasing a dwell time of the galvo-mirror assembly if the number of pulses per burst is increased and, otherwise, decreasing the dwell time.

9. The system of claim 1, wherein:
the characteristic comprises a width of a pulse; and
the controller adjusts the rate of movement by increasing a dwell time of the galvo-mirror assembly if the pulse width is increased and, otherwise, decreasing the dwell time.

10. The system of claim 1, wherein:
the characteristic comprises a number of pulses per burst of pulses; and
the controller adjusts the rate of movement by increasing a scanning speed of the galvo-mirror assembly if the number of pulses per burst is increased and, otherwise, decreasing the scanning speed.

11. The system of claim 1, wherein:
the characteristic comprises a number of pulses per burst of pulses; and
the controller adjusts the rate of movement by decreasing a scanning speed of the galvo-mirror assembly if the number of pulses per burst is increased and, otherwise, increasing the scanning speed.

12. The system of claim 1, wherein:
the characteristic comprises a duration of time between consecutive bursts of pulses; and
the controller adjusts the rate of movement by increasing a scanning speed of the galvo-mirror assembly if the duration of time between consecutive bursts of pulses is increased and, otherwise, decreasing the scanning speed.

13. The system of claim 1, wherein:
the characteristic comprises a duration of time between consecutive bursts of pulses; and
the controller adjusts the rate of movement by decreasing a scanning speed of the galvo-mirror assembly if the duration of time between consecutive bursts of pulses is increased and, otherwise, increasing the scanning speed.

14. The system of claim 1, wherein:
the characteristic comprises a pulse repetition rate; and
the controller adjusts the rate of movement by increasing a scanning speed of the galvo-mirror assembly if the pulse repetition rate is increased and, otherwise, decreasing the scanning speed.

15. The system of claim 1, wherein:
the characteristic comprises a pulse repetition rate; and
the controller adjusts the rate of movement by decreasing a scanning speed of the galvo-mirror assembly if the pulse repetition rate is increased and, otherwise, increasing the scanning speed.

16. The system of claim 1, wherein:
the characteristic comprises a width of pulses; and
the controller adjusts the rate of movement by increasing a scanning speed of the galvo-mirror assembly if the pulses width is increased and, otherwise, decreasing the scanning speed.

17. The system of claim 1, wherein:
the characteristic comprises a width of pulses; and
the controller adjusts the rate of movement by decreasing a scanning speed of the galvo-mirror assembly if the pulses width is decreased and, otherwise, increasing the scanning speed.

18. A method for operating a laser-based dental treatment system, the method comprising the steps of:
  generating a sequence of laser beam pulses;
  adjusting at least one characteristic of the sequence of pulses based on an operator interaction with a variable input device while the sequence of pulses is being directed to a first irradiation location of a selected treatment area; and
  while the sequence of pulses is being directed to the selected treatment area, adjusting with a controller, automatically and as a function of the at least one adjusted characteristic, a rate of movement of a galvo-mirror assembly such that a size of a next irradiation location after adjustment is made relative to a size of the first irradiation location is unchanged.

19. The method of claim 18, wherein:
  the step of adjusting the characteristic comprises one of increasing and decreasing a burst duration; and
  the step of adjusting the rate of movement comprises increasing a dwell time of the galvo-mirror assembly if the burst duration is increased and, otherwise, decreasing the dwell time.

20. The method of claim 18, wherein:
  the step of adjusting the characteristic comprises one of increasing and decreasing a duration of time between consecutive bursts of pulses; and
  the step of adjusting the rate of movement comprises increasing a jump interval of the galvo-mirror assembly if the duration of time between consecutive bursts of pulses is increased and, otherwise, decreasing the jump interval.

21. The method of claim 18, wherein:
  the step of adjusting the characteristic comprises one of increasing and decreasing a number of pulses per burst of pulses; and
  the step of adjusting the rate of movement comprises increasing a dwell time of the galvo-mirror assembly if the number of pulses per burst is increased and, otherwise, decreasing the dwell time.

22. The method of claim 18, wherein:
  the step of adjusting the characteristic comprises one of increasing and decreasing a width of a pulse; and
  the step of adjusting the rate of movement comprises increasing a dwell time of the galvo-mirror assembly if the pulse width is increased and, otherwise, decreasing the dwell time.

23. The method of claim 18, wherein:
  the step of adjusting the characteristic comprises one of increasing and decreasing a number of pulses per burst of pulses; and
  the step of adjusting the rate of movement comprises increasing a scanning speed of the galvo-mirror assembly if the number of pulses per burst is increased and, otherwise, decreasing the scanning speed.

24. The method of claim 18, wherein:
  the step of adjusting the characteristic comprises one of increasing and decreasing a number of pulses per burst of pulses; and
  the step of adjusting the rate of movement comprises decreasing a scanning speed of the galvo-mirror assembly if the number of pulses per burst is increased and, otherwise, increasing the scanning speed.

25. The method of claim 18, wherein:
  the step of adjusting the characteristic comprises one of increasing and decreasing a duration of time between consecutive bursts of pulses; and
  the step of adjusting the rate of movement comprises increasing a scanning speed of the galvo-mirror assembly if the duration of time between consecutive bursts of pulses is increased and, otherwise, decreasing the scanning speed.

26. The method of claim 18, wherein:
  the step of adjusting the characteristic comprises one of increasing and decreasing a duration of time between consecutive bursts of pulses; and
  the step of adjusting the rate of movement comprises decreasing a scanning speed of the galvo-mirror assembly if the duration of time between consecutive bursts of pulses is increased and, otherwise, increasing the scanning speed.

27. The method of claim 18, wherein:
  the step of adjusting the characteristic comprises one of increasing and decreasing a pulse repetition rate; and
  the step of adjusting the rate of movement comprises increasing a scanning speed of the galvo-mirror assembly if the pulse repetition rate is increased and, otherwise, decreasing the scanning speed.

28. The method of claim 18, wherein:
  the step of adjusting the characteristic comprises one of increasing and decreasing a pulse repetition rate; and
  the step of adjusting the rate of movement comprises decreasing a scanning speed of the galvo-mirror assembly if the pulse repetition rate is increased and, otherwise, increasing the scanning speed.

29. The method of claim 18, wherein:
  the step of adjusting the characteristic comprises one of increasing and decreasing a width of pulses; and
  the step of adjusting the rate of movement comprises increasing a scanning speed of the galvo-mirror assembly if the pulses width is increased and, otherwise, decreasing the scanning speed.

30. The method of claim 18, wherein:
  the step of adjusting the characteristic comprises one of increasing and decreasing a width of pulses; and
  the step of adjusting the rate of movement comprises decreasing a scanning speed of the galvo-mirror assembly if the pulses width is decreased and, otherwise, increasing the scanning speed.

* * * * *